United States Patent [19]

Noyori et al.

[11] 4,315,032
[45] Feb. 9, 1982

[54] PROCESS FOR PREPARATION OF ADJACENTLY DISUBSTITUTED KETONES

[75] Inventors: Ryoji Noyori, Aichi; Masaaki Suzuki, Nagoya; Seizi Kurozumi, Hino, all of Japan

[73] Assignee: Teitin Limited, Osaka, Japan

[21] Appl. No.: 149,584

[22] Filed: May 14, 1980

[30] Foreign Application Priority Data

May 18, 1979 [JP] Japan ................................ 54/60293

[51] Int. Cl.³ .................. C07C 177/00; C07C 45/69; C07C 45/70; C07C 45/72
[52] U.S. Cl. .................................. 424/317; 560/121; 562/503; 536/103; 424/305; 568/345; 568/346; 568/347; 568/390; 568/391; 568/313; 568/314; 568/315; 556/441; 260/345.7 P; 260/345.8 P; 542/426
[58] Field of Search .................. 560/121; 562/503; 424/305, 317; 542/426; 556/441; 260/345.7 P, 345.8 P

[56]  References Cited

U.S. PATENT DOCUMENTS 4,131,738 12/1978 Smith .................... 560/121

OTHER PUBLICATIONS

Tanaka et al., Tetrahedron Letters, 1535 (1975).

*Primary Examiner*—Robert Gerstl

*Attorney, Agent, or Firm*—Sherman & Shalloway

[57]  ABSTRACT

A novel 7-hydroxyprostaglandin $E_1$, or a stereoisomer thereof, or a protected derivative thereof, having the following formula:

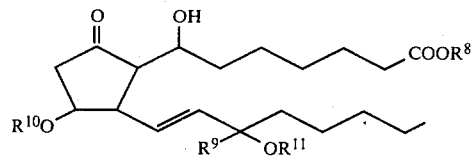

wherein $R^8$ represents H, $CH_3$ or $C_2H_5$, $R^9$ represents H or $CH_3$, $R^{10}$ and $R^{11}$ are identical or different, and each represents H, tetrahydropyranyl or t-butyldimethylsilyl. Also provided is a process for producing an adjacently disubstituted ketone including the above compounds, i.e. 7-oxoprostaglandin, etc. which comprises reacting an $\alpha,\beta$-unsaturated carbonyl compound with a cuprous salt and an organolithium compound in an aprotic inert organic medium in the presence of trialkylphosphine, the amounts of said cuprous salt and said organolithium compound being substantially equimolar, and reacting the product with a protected acetal derivative of an organic carbonyl compound or an aldehyde in the presence of a Lewis acid, if necessary, followed by reacting the product with a proton donor.

6 Claims, No Drawings

PROCESS FOR PREPARATION OF ADJACENTLY DISUBSTITUTED KETONES

This invention relates to a process for preparing adjacently disubstituted ketones. This invention also pertains certain novel prostagladins $E_1$ or the stereoisomers thereof produced by the process of invention, and to anti-thrombotic compositions containing these prostaglandins as active ingredients.

Methods have previously been known to obtain ketones having substituents at the $\alpha$- and $\beta$-positions of $\alpha,\beta$-unsaturated carbonyl compounds by reacting the $\alpha,\beta$-unsaturated carbonyl compounds with organocopper compounds and capturing the resulting enolates by various reagents. These methods include, for example, (1) A method which comprises reacting an $\alpha,\beta$-unsaturated carbonyl compound with a homo-cuprate expressed by the formula $R_2CuLi$, capturing the resulting enolate by a silylating agent, again converting the resulting enol silylether into an enolate using a base such as lithium amide, and then reacting the enolate with an alkyl halide to capture it [J. H. Fried et al., Journal of Organic Chemistey, 39, 2506 (1974)].

(2) A method which comprises reacting an $\alpha,\beta$-unsaturated carbonyl compound with a homo-cuprate or mixed cuprate expressed by the formula $R_2CuLi$ or $RR'CuLi$, and directly capturing the resulting enolate by an alkyl halide [J. H. Posner et al., Journal of American Chemical Society, 97, 107, (1975)].

(3) A method which comprises reacting an $\alpha,\beta$-unsaturated carbonyl compound with a complex of an organic triphosphine and a homo-cuprate expressed by the formula $R_2CuLi$, and directly capturing the resulting enolate by formaldehyde [J. Stork et al., Jornal of American Chemical Society, 97, 6260 (1975)].

(4) A method which comprises reacting an $\alpha,\beta$-unsaturated carbonyl compound with a complex of a homo-cuprate expressed by the formula $R_2CuLi$ and an organic triphosphine, and capturing the resulting enolate by an acid chloride [S. Kurozumi et al., Tetrahedron Letter, 19, 1535 (1975)].

These methods, however, have the defect that there is a limitation to a range of $\alpha,\beta$-unsaturated carbonyl compounds which can be used, or $R_2CuLi$ or $RR'CuLi$ and an alpha-position substituent introducing agent such as an acid chloride must be used in a considerably excessive amount over the stoichiometrical amount with respect to the $\alpha,\beta$-unsaturated carbonyl compound, or the yield of the desired final compound is generally low.

Recently, method for producing an $\alpha$-($\alpha$-hydroxyalkyl)-$\beta$-alkyl substituted ketone was reported which comprises reacting an $\alpha,\beta$-unsaturated carbonyl compound with a homodialkyl cuprate of the formula $R_2CuLi$, and reacting the resulting product further with an aldehyde in the presence of $ZnCl_2$ [Tetrahedron Letters, 35, 425-435 (1979)]. This method is noteworthy because although the aldehyde and homodialkyl cuprate are used generally in excessive amounts over the $\alpha,\beta$-unsaturated carbonyl compound, certain desired compounds can be obtained in high yields based on the $\alpha,\beta$-unsaturated carbonyl compound used. However, according to this method, the range of usable $\alpha,\beta$-unsaturated carbonyl compounds is still limited, or the yield of the final product based on the dialkyl cuprate is still at a low level. Also, protected acetals do not react in this reaction system. Hence, this prior method still leaves room for improvement.

It is an object of this invention therefore to provide a novel process for producing adjacently disubstituted ketones.

Another object of this invention is to provide a process which can afford various adjacently disubstituted ketones when applied to a broad range of $\alpha,\beta$-unsaturated carbonyl compounds.

Still another object of this invention is to provide a process in which an $\alpha$-position substituent introducing agent and a $\beta$-position substituent introducing agent can be used substantially in stoichiometrical amounts with respect to an $\alpha,\beta$-unsaturated carbonyl compound, and which, therefore, can give an adjacently disubstituted ketones in a high yield both based on any of these reagents.

Yet another object of this invention is to provide a process which can afford adjacently disubstituted ketones in high yields from cyclopent-2-en-1-ones and cyclohex-2-en-1-ones, especially the substituted derivatives thereof.

Still another object of this invention is to provide 7-hydroxyprostaglandin $E_1$, the stereoisomers thereof, and the protected derivatives thereof, which are novel compounds.

A further object of this invention is to provide an anti-thrombotic composition or drug comprising as an active ingredient 7-hydroxyprostaglandin $E_1$ or its stereoisomer.

Other objects and advantages of this invention will become apparent from the following description.

According to this invention, these objects and advantages are achieved firstly by a process for producing an adjacently disubstituted ketone expressed by the following formula (5)-a

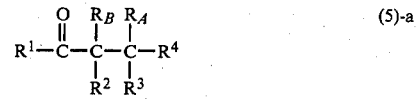

wherein $R^1$, $R^2$, $R^3$ and $R^4$ are identical or different, and represent a hydrogen atom or an organic group having 1 to 20 carbon atoms, or any two of these groups $R^1$, $R^2$, $R^3$ and $R^4$ may be linked to each other to form a ring, $R_A$ represents an organic group having 1 to 20 carbon atoms, and $R_B$ represents a group derived from a protected acetal derivative of an organic carbonyl compound expressed by formula (4)-a below, and when $R^6$ in formula (4)-a represents a hydrogen atom, an organic group having 1 to 20 carbon atoms or

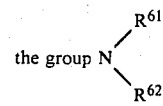

in which $R^{61}$ and $R^{62}$ are identical or different and represent a hydrogen atom or an organic group having 1 to 20 carbon atoms or $R^{61}$ and $R^{62}$ may be linked to each other to form a ring, $R_B$ represents a group resulting from the removal of the group $-OR^7$ from formula (4)-a, and where $R^6$ in formula (4)-a represents $-O-$ ($C_1$-$C_{20}$ organic group) and $R^7$ represents an organic group having 1 to 20 carbon atoms, $R_B$ represents a group resulting from the removal of the group $-OR^7$ or —$R^6$, provided that when two $R^7$ groups are bonded to each other to form a 5- or 6-membered ring, $R_B$ represents a group resulting from the removal of the group —$R^6$ from formula (4)-a, or a group of the following formula

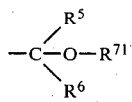

in which $R^5$ and $R^6$ are as defined below and $R^{71}$ represents a β- or γ-hydroxyalkyl group, which comprises reacting an α,β-unsaturated carbonyl compound expressed by the following formula (1)

 (1)

wherein $R^1$, $R^2$, $R^3$ and $R^4$ are as defined above, with a cuprous salt of the following formula (2)

$$CuX \qquad (2)$$

wherein X represents a monovalent anion, and an organolithium compound of the following formula (3)

$$R_A Li \qquad (3)$$

wherein $R_A$ is as defined above, in an aprotic inert organic medium in the presence of a trialkylphosphine, the amounts of said cuprous salt and said organolithium compound being substantially equimolar, and thereafter reacting the product with a protected acetal derivative of an organic carbonyl compound having the following formula (4)-a

 (4)-a wherein $R^5$ represents a hydrogen atom or an organic group having 1 to 20 carbon atoms, and $R^6$ represents a hydrogen atom, an organic group having 1 to 20 carbon atoms, —O—(C$_1$-C$_{20}$ organic group), or an amino group of the following formula

in which $R^{61}$ and $R^{62}$ are as defined above, $R^7$ represents an organic group having 1 to 20 carbon atoms or two $R^7$ groups may be linked to each other to form a 5- or 6-membered ring together with the two oxygen atoms to which they are bonded and the carbon atom to which the two $OR^7$ groups are bonded, and $R^7$ and $R^5$ may be linked to each other to form a 5- or 6-membered ring, in the presence of a Lewis acid.

The essence of the process of this invention consists of a first reaction wherein the α,β-unsaturated carbonyl compound reacts with the organic mono-copper compound in the presence of the trialkylphosphine to form the corresponding β-substituted enol cuprate having low reactivity, and a second reaction wherein the enol cuprate having low reactivity and the protected acetal derivative of an organic carbonyl compound are activated and reacted in the presence of a Lewis acid to form the corresponding α,β-adjacently disubstituted ketone.

A reaction between such a β-substituted enol cuprate having low reactivity and the protected acetal derivative of an organic carbonyl compound has not been known heretofore. It is to the inventors' surprise, too, that this reaction proceeds in the presence of a Lewis acid and can be applied to various β-substituted enol cuprates to form α,β-adjacently disubstituted ketones to high yields.

These reactions in accordance with this invention can be schematically shown as follows:

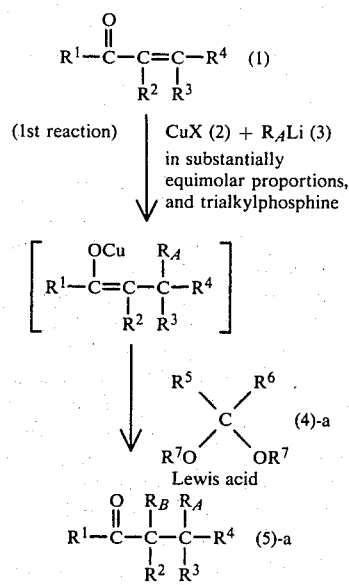

Possibly, the parenthesized intermediate in the above reaction scheme, i.e. the β-substituted enol cuprate, undergoes coordination by the trialkylphosphine or LiX in the reaction system. In the above reaction scheme, $R_B$ in formula (5)-a is a group derived from the compound of formula (4)-a.

When an aldehyde is used instead of the protected acetal derivative of an organic carbonyl compound, the present invention provides a process for producing an adjacently disubstituted ketone of the following formula (5)-b

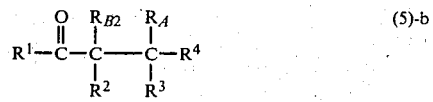 (5)-b wherein $R^1$, $R^2$, $R^3$, $R^4$ and $R_A$ are as defined are as defined hereinabove with respect to formula (1), and $R_{B2}$ represents a group of the formula

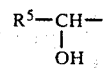

in which $R^5$ is as defined above with regard to formula (4)-a, which comprises (1) performing the aforesaid first reaction, and thereafter (2) reacting the product with an aldehyde of the formula (4)-b

     (4)-b wherein $R^5$ is as defined above, in the presence of a Lewis acid and further reacting the product with a proton donor (second reaction).

Likewise, the present invention further provides a process for producing an adjacently disubstituted ketone of the following formula (5)-c

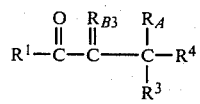     (5)-c wherein $R^1$, $R^3$, $R^4$ and $R_A$ are as defined with regard to formula (1), and $R_{B3}$ represents a group derived from a protected acetal derivative of an organic carbonyl compound having formula (4)-a, and when $R^6$ in formula (4)-a represents a hydrogen atom, an organic group having 1 to 20 carbon atoms or a group of the formula

in which $R^{61}$ and $R^{62}$ are defined above, $R_{B3}$ represents a group of the formula

and when $R^6$ in formula (4)-a represents $-O-$ ($C_1$-$C_{20}$ organic group) and $R^7$ represents an organic group having 1 to 20 carbon atoms, $R_{B3}$ represents a group of the formula

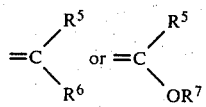

provided that two $R^7$ groups are linked to each other to form a 5- or 6-membered ring, $R_{B3}$ represents a group of the formula

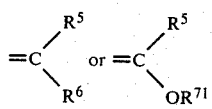

in which $R^{71}$ represents a $\beta$- or $\gamma$-hydroxyalkyl group, which comprises performing the first reaction using an $\alpha,\beta$-unsaturated carbonyl compound of the following formula (1)-a

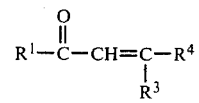     (1)-a wherein $R^1$, $R^3$ and $R^4$ are as defined above with regard to formula (1), performing the second reaction using the protected acetal derivative of an organic carbonyl compound having formula (4)-a, and thereafter treating the reaction product in a manner known per se.

The reactions in accordance with this invention are described below in detail.

[FIRST REACTION].

In formula (1) representing the $\alpha,\beta$-unsaturated carbonyl compound uses as a starting material in this invention, $R^1$, $R^2$, $R^3$ and $R^4$ are identical with, or different from, each other, and represent a hydrogen atom or an organic group having 1 to 20 carbon atoms, and any two of the groups $R^1$, $R^2$, $R^3$ and $R^4$ may be linked to each other to form a ring, preferably a 5- or 6-membered ring. Examples of preferred organic groups having 1 to 20 carbon atoms include alkyl groups having 1 to 15 carbon atoms such as methyl, ethyl, propyl, hexyl, decyl or pentadecyl, alkenyl groups having 3 to 6 carbon atoms such as 2-propenyl or 3-hexenyl and aralkyl groups having 7 or 8 carbon atoms such as benzyl or $\beta$-phenylethyl. Alkylene groups having 2 to 10 carbon atoms such as ethylene, trimethylene, pentamethylene or decamethylene are preferred as divalent groups in the case of any two of these groups $R^1$ to $R^4$ forming a ring. These organic groups may have substituents which are inert under the reaction conditions.

Such substituents are these organic groups include alkyl, alkenyl, aralkyl, alkoxy, alkylsiloxy and ester groups as preferred species. Preferred alkyl groups are those having 1 to 10 carbon atoms such as methyl, ethyl, butyl or decyl. Preferred alkenyl groups are those having 1 to 10 carbon atoms such as 1-ethenyl, 2-propenyl and 1-octenyl. Preferred aralkyl groups are those having 7 to 10 carbon atoms. Preferred alkoxy groups are those having 1 to 10 carbon atoms such as methoxy, ethoxy, t-butoxy, tetrahydropyranyloxy or $\alpha$-ethoxyethoxy. Preferred alkylsiloxy groups are those in which each alkyl group has 1 to 20 carbon atoms, such as t-butyldimethylsiloxy or benzyldimethylsiloxy. Preferred ester groups are those having 2 to 10 carbon atoms such as methoxycarbonyl, ethoxycarbonyl or t-butoxycarbonyl.

Typical examples of the $\alpha,\beta$-unsaturated carbonyl compound are given below.

1-A

Examples of linear compounds in which $R^1$, $R^2$, $R^3$ and $R^4$ are not linked to each other Methyl vinyl ketone,
ethyl vinyl ketone,
n-propyl vinyl ketone,
n-butyl vinyl ketone,
isobutyl vinyl ketone,
n-amyl vinyl ketone,
methyl isopropenyl ketone,
ethyl isopropenyl ketone,
2-ethyl-1-hexen-3-one,
3-penten-2-one, 3-hexen-2-one,
3-hepten-2-one,
7-methyl-5-octen-4-one,
5,5-dimethyl-3-hexen-2-one,
4-methyl-3-penten-2-one,
5-methyl-4-hexen-3-one,
5-ethyl-4-hepten-3-one,
3-methyl-3-hepten-2-one,
3-ethyl-3-hepten-2-one,
3-n-propyl-3-hexen-2-one,
3,4-dimethyl-3-penten-2-one,
4,5-dimethyl-4-penten-2-one,
2,4,5-trimethyl-4-hexen-3-one,
acrolein,
crotonaldehyde,
methacrolein,
2-methyl-2-butenal, and
2,3-dimethyl-2-butenal.

1-B

Examples of compounds in which $R^1$ is linked to $R^3$ (or $R^4$) to form a ring (a) Five-membered cyclic compounds
Cyclopent-2-en-1-one,
3,4-dimethylcyclopent-2-en-1-one,
3,4,4-trimethylcyclopent-2-en-1-one,
2-methylcyclopent-2-en-1-one,
3-methylcyclopent-2-en-1-one,
4-methylcyclopent-2-en-1-one,
3-isopropylcyclopent-2-en-1-one,
2,3,4-trimethylcyclopent-2-en-1-one,
4-isopropyl-2,3-dimethylcyclopent-2-en-1-one,
3-ethyl-2-methylcyclopent-2-en-1-one,
2,3-dimethylcyclopent-2-en-1-one,
3-methyl-2-amylcyclopent-2-en-1-one,
1(8)-hydroinden-2-one,
8(9)-hydroinden-1-one,
2-hydroinden-1-one, and
4-t-butyldimethylsiloxy-cyclopent-2-en-1-one.

(b) Six-membered compounds
Cyclohex-2-en-1-one,
2-methylcyclohex-2-en-1-one,
3-methylcyclohex-2-en-1-one,
isophorone, (i.e., 3,5,5-trimethyl-2-cyclohexen-1-one),
carvone,
2,3-dimethylcyclohex-2-en-1-one,
2-keto-1-methyl-$\Delta^3$-octalin,
1-keto-$\Delta^2$-octalin,
1(5)-androtene-3,17-dione, and
5-pregnen-3-ol-7,20-dione acetate.

(c) Seven-membered cyclic compounds
Cyclohept-2-en-1-one,
2-methylcyclohept-2-en-1-one, and
3,7-dimethylcyclohept-2-en-1-one.

1-C

Examples of compounds in which $R^1$ is linked to $R^2$ to form a ring

2-Methylenecyclopentan-1-one,
2-methylenecyclohexan-1-one, and
2-pyrrolidinecycloheptan-1-one.

1-D

Examples of compounds in which $R^2$ is linked to $R^3$ (or $R^4$) to form a ring 1-Acetylcyclopentene,
1-cyclopentenaldehyde,
1-acetylcyclohexene,
1-cyclohexenaldehyde, and
1-acetylcycloheptene.

The cuprous salt used in this invention is expressed by the formula $$CuX \qquad (2)$$

wherein X represents monovalent anion.

Inorganic anions are preferred as the anion for X. Examples are halogen ions such as chlorine, bromine or iodine ions, and a cyanide ion.

Examples of the cuprous salt include cuprous chloride, cuprous bromide, cuprous iodide and cuprous cyanide.

The organolithium compound used in this invention is expressed by the following formula $$R_A Li \qquad (3)$$

wherein $R_A$ represents an organic group having 1 to 20 carbon atoms.

Examples of the organic group having 1 to 20 carbons represented by $R_A$ include alkyl groups, alkenyl groups, alkynyl groups, aralkyl groups, aralkenyl groups, aralkynyl groups, alkoxyalkyl groups, alkoxyalkenyl groups, alkoxyalkynyl groups, siloxyalkyl groups, siloxyalkenyl groups, and siloxyalkynyl groups.

Specific examples of the organolithium compound include alkyl lithiums such as methyllithium, ethyllithium, n-propyllithium, isopropyllithium, n-butyllithium, t-butyllithium, n-pentyllithium, n-hexyllithium, cyclohexyllithium, n-heptyllithium, n-octyllithium and n-nonyllithium; alkenyl lithiums such as vinyllithium, 1-lithio-prop-cis-1-ene, 1-lithio-prop-trans-1-ene, 1-lithio-oct-cis-5-ene, 1-lithio-oct-trans-5-ene, 1-lithio-oct-cis-1-ene and 1-lithio-oct-trans-1-ene; alkynyllithiums such as 1-lithio-oct-5-yne, 1-lithio-but-1-yne, 1-lithio-pent-1-yne, 1-lithio-hex-1-yne, 1-lithio-hept-1-yne and 1-lithio-oct-1-yne; aralkyllithiums such as 1-lithio-8-phenyl-octene; aralkenyllithiums such as 1-(2-phenyl)-vinyllithium, 1-lithio-8-phenyl-oct-trans-1-ene and 1-lithio-8-phenyl-oct-cis-1-ene; aralkynyllithiums such as 1-lithio-8-phenyl-oct-5-yne; alkoxyalkyllithiums such as 1-lithio-3-tetrahydropyranyloxy-octane and 1-lithio-bis-(3,7-tetrahydropyranyloxy)-octane; alkoxy alkenyllithiums such as 1-lithio-3-tetrahydropyranyloxy-oct-trans-1-ene, 1-lithio-bis(3,7-tetrahydropyranyloxy-oct-trans-1-ene, and 1-lithio-3-tetrahydropyranyloxy-oct-trans-1-cis-5-diene; alkoxyalkynyllithiums such as 1-lithio-3-($\alpha$-ethoxy)-ethoxy-oct-5-yne; siloxyalkenyllithiums such as 1-lithio-3-t-butyldimethylsiloxy-oct-trans-1-ene; siloxyalkyllithiums such as 1-lithio-3-t-butyldimethylsiloxy-octane; and siloxyalkynyllithiums such as 1-lithio-3-t-butyldimethylsiloxy-oct-5-yne.

The first reaction in accordance with this invention is carried out by reacting the $\alpha,\beta$-unsaturated carbonyl compound with the cuprous salt and organolithium compound in an aprotic inert organic medium in the presence of a trialkylphosphine.

In this reaction, the cuprous salt and the organolithium compound are used in substantially equimolar proportions, and preferably 0.9 to 1.2 moles, especially preferably 0.95 to 1.15 moles, of the cuprous salt is used per mole of the organolithium compound.

It is believed that this reaction proceeds by a mechanism whereby the cuprous salt and the organolithium compound used in nearly equimolar proportions first form a complex under the influence of the trialkylphosphine present in the reaction system, and the resulting complex then reacts with the α,β-unsaturated carbonyl compound.

Typically, the reaction of forming the complex is considered to be schematically shown as follows:

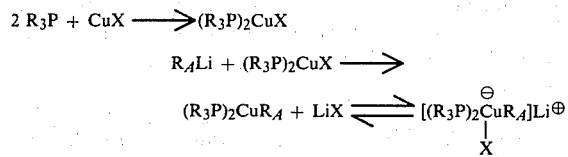

Thus, stoichiometrically, 1 mole of the cuprous salt reacts with 1 mole of the organolithium compound to form a complex comprising a copper atom and one monovalent organic group including the trialkylphosphine ($R_3P$) as a ligand.

The first reaction in which the cuprous salt and the organolithium compound are used in nearly equimolar proportions and the resulting complex comprising a copper atom and one monovalent organic group ($R_A$) is reacted with the α,β-unsaturated carbonyl compound has the advantage that the monovalent organic group of the complex is effectively used in the reaction. This can be understood from the fact that in the case of a homocuprate or mixed cuprate such as $R_2CuLi$ or $RR'CuLi$ used in the aforesaid prior art, only one of the two organic groups (2R or R and R') is effectively utilized in the reaction.

The amount of the trialkylphosphine used in the process of this invention is 1 to 3 moles, preferably 1.9 to 2.2 moles.

Tri($C_1$-$C_6$) alkyl)phosphines such as trimethylphosphine, triethylphosphine, tri-n-propylphosphine, tri-n-butylphosphine or tri-n-hexylphosphine are preferred. Tri-n-butylphosphine is especially preferred.

Examples of the aprotic inert organic medium include saturated hydrocarbons such as pentane, hexane, heptane and cyclohexane; aromatic hydrocarbons such as benzene, toluene and xylene; ethers such as diethyl ether, tetrahydrofuran, dioxane, dimethoxyethane, diethylene glycol and dimethyl ether; and so-called aprotic polar solvents such as hexamethylphosphoric triamide, N,N-dimethylformamide, N,N-dimethylacetamide, dimethyl sulfoxide, sulfolane and N-methylpyrrolidone. If desired, two or more of these aprotic inert organic media can be used together.

Advantageously, the reaction is usually carried out by adding the cuprous salt, the organolithium compound and the trialkylphosphine to the aprotic inert organic medium in any desired sequence, treating them in an atmosphere of an inert gas such as nitrogen or argon at a low temperature of, say, room temperature to −100° C., preferably −40° C. to −78° C., and then adding a predetermined amount of the α,β-unsaturated carbonyl compound to the reaction mixture.

The amount of the α,β-unsaturated carbonyl compound is preferably 0.5 to 2 moles, especially preferably 0.8 to 1.2 moles, per mole of the organolithium compound. The reaction of introducing an organic group into the α,β-unsaturated carbonyl compound is likewise carried out in an inert atmosphere such as nitrogen or argon at low temperatures of, for example, room temperature to −100° C., preferably 5° C. to −78° C. Usually, the reaction comes to an end in several hours.

Thus, according to the first reaction of this invention, a β-substituted enol cuprate results from the introduction of the organic group ($R_A$) derived from the organolithium compound into the β-position of the α,β-unsaturated carbonyl compound.

The β-substituted enol cuprate has low reactivity, and therefore, it has not been known in the past that this compound can be reacted with a neutral compound such as a protected acetal derivative of an organic carbonyl compound. According to this invention, such a β-substituted enol cuprate having low reactivity can be reacted with a neutral compound by the second reaction to produce an α,β-adjacently disubstituted ketone.

Another advantage of the second reaction in accordance with this invention is that the β-substituted enol cuprate has low reactivity and therefore is relatively stable, but since conditions sufficient for it to react with a neutral compound at low temperatures are given by the second reaction, the reaction can be performed under such conditions that the β-substituted enol cuprate does not undergo isomerization, i.e. transfer of its double bond does not occur, and therefore, the desired adjacently disubstituted ketone can be produced selectively in high yields.

[Second Reaction]

The second reaction in this invention is characterized by the fact that an α-substituent is introduced in the presence of a Lewis acid into the β-substituted enol cuprate formed by the first reaction described hereinabove.

Accordingly, the second reaction is carried out by reacting the β-substituted enol cuprate with a protected acetal derivative of an organic carbonyl group having the following formula (4)-a

wherein $R^5$ represents a hydrogen atom or an organic group having 1 to 20 carbon atoms, $R^6$ represents a hydrogen atom, an organic group having 1 to 20 carbon atom, —O—($C_1$-$C_{20}$ organic group), or an amino group of the formula

in which $R^{61}$ and $R^{62}$ are identical or different and represent a hydrogen atom or an organic group having 1 to 20 carbon atoms, or $R^{61}$ and $R^{62}$ may be linked to each other to form a ring, $R^7$ represents an organic group having 1 to 20 carbon atoms or two $R^7$ groups may be linked to each other to form a 5- or 6-membered ring together with the two oxygen atoms to which they are bonded and the carbon atom to which the $OR^7$ groups are bonded, and $R^7$ and $R^5$ may be linked to each other to form a 5- or 6-membered ring,
in the presence of a Lewis acid; or by reacting the β-substituted enol cuprate with an aldehyde of the following formula (4)-b

  (4)-b wherein $R^5$ represents a hydrogen atom or an organic group having 1 to 20 carbon atoms,
in the presence of a Lewis acid, and then reacting the product with a proton donor.

Boron trifluoride, a boron trifluoride-ether complex, aluminum chloride and titanium tetrachloride are preferred as the Lewis acid used in the second reaction because these compounds give the final product in high yields. Boron trifluoride and boron trifluorideether complex are especially preferred.

The Lewis acid can be added to the reaction mixture obtained in the first reaction and containing the resulting β-substituted enol cuprate before submitting it to the second reaction. Or it may also be added during the performance of the first reaction. The amount of the Lewis acid is preferably 0.7 to 1.3 mlles, especially preferably 0.9 to 1.1 moles, per mol of the cupric salt used in the first reaction.

The second reaction is carried out desirably in an inert atmosphere such as nitrogen or argon at a temperature of preferably 50° C. to −100° C., especially room temperature to −78° C. The reaction usually comes to an end within several hours.

The reaction involving using the protected acetal derivative of an organic carbonyl compound having the following formula (4)-a gives an adjacently disubstituted ketone of the following formula (5)-a

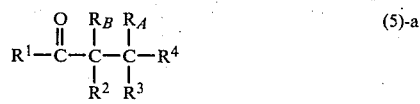 (5)-a wherein $R^1$, $R^2$, $R^3$, $R^4$ and $R_A$ are as defined hereinabove, and $R_B$ represents a group derived from the protected acetal derivative of an organic carbonyl compound having formula (4)-a, and when $R^6$ in formula (4)-a represents a hydrogen atom, an organic group having 1 to 20 carbon atoms or a group of the formula

in which $R^{61}$ and $R^{62}$ are as defined above, $R_B$ represents a group resulting from the removal of the group —$OR^7$ from formula (4)-a, and when $R^6$ in formula (4)-a represents —O—($C_1$-$C_{20}$ organic group) and $R^7$ represents an organic group having 1 to 20 carbon atoms, $R_B$ represents a group resulting from the removal of the group —$OR^7$ or —$R^6$ from formula (4)-a, provided that when two $R^7$ groups are linked to each other to form a 5- or 6-membered ring, $R_B$ represents a group resulting from the removal of the group —$R^6$ from formula (4)-a or a group of the formula

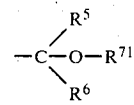

in which $R^5$ and $R^6$ are as defined hereinabove, and $R^{71}$ represents a β- or γ-hydroxyalkyl group.

The organic groups in the definitions of $R^5$, $R^6$ and $R^7$ in formula (4)-a are the same as those in formula (1) exemplified hereinabove with regard to the first reaction.

Preferred organic groups having 1 to 20 carbon atoms in $R^5$ and $R^6$ may be the same as the preferred organic groups in formula (1). As the organic group having 1 to 20 carbon atoms for $R^7$, lower alkyl groups having 1 to 4 carbon atoms such as methyl, ethyl or n-butyl, alkylene groups having 2 or 3 carbon atoms participating in the formation of a 5- or 6-membered ring, which are formed by the linking of two $R^7$, are preferred.

As is seen from the definitions of $R^5$ and $R^6$, the protected acetal derivatives of organic carbonyl compounds having formula (4)-a include protected acetal derivatives of aldehydes (in which at least one of $R^5$ and $R^6$ is a hydrogen atom), protected acetal derivatives of ketones (in which both $R^5$ and $R^6$ are organic groups having 1 to 20 carbon atoms), protected acetal derivatives of esters [in which $R^6$ is —O—($C_1$-$C_{20}$ organic group)], and acetal protected acetal derivative of amides

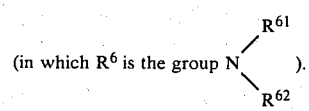

Examples of these protected acetal derivatives of organic carbonyl compounds are given below.

Protected acetal derivatives of aldehydes

Protected acetal derivatives, preferably those in which the carbonyl group is protected by a lower alkyl group having 1 to 4 carbon atoms, an ethylene group or a trimethylene group, of aldehydes such as formaldehyde, acetaldehyde, crotonaldehyde, n-hexanal, n-nonanal, n-decanal, 1-pentanal, cyclopentylaldehyde, cyclohexylaldehyde, 2-probenal, 2-butenal, 3-pentenal, 3-octenal, 2-propynal, 2-butynal, benzaldehyde, cinnamaldehyde, α-phenylacetaldehyde, β-phenylpropanal, α-methoxyacetaldehyde, malonedialdehyde monoethylene acetal, β-benzyloxypropionaldehyde, ω-ethoxycarbonylpentanal, ω-methoxycarbonyl-3-pentenal, ω-methoxycarbonylhexanal, ω-methoxycarbonyl-5-hexenal, 6-tetrapyranyloxyhexanal, 6-tetrapyranyloxy-3-hexenal, 3-oxobutanal and n-butyl glyoxalate.

Protected acetal derivatives of ketones

Protected acetal derivatives, preferably those in which the carbonyl group is protected by a lower alkyl group having 1 to 4 carbon atoms, an ethylene group or a trimethylene group, of ketones such as acetone, methyl ethyl ketone, 2-pentanone, 2-hexanone, 3-hexanone, 5-hexen-2-one, 4-decanone, 7-methoxycarbonyl-2-heptanone, cyclopentanone, cyclohexanone, cycloheptanone, cyclohexyl methyl ketone, acetophenone, benzophenone, benzyl methyl ketone, p-methoxyacetophenone and α-ethoxyacetophenone.

Protected acetal derivatives of esters

Methyl ortho-formate, ethyl ortho-formate, triethyl ortho-acetate, trimethyl ortho-acetate, 1,1,1-triethoxypropane, 1,1,1-trimethoxypropane, 1,1,1-triethoxybutane, 1,1,1-trimethoxybutane, 1,1,1-triethoxypentane, 1,1,1-trimethoxypentane, 1,1,1-triethoxyhexane, 1,1,1-trimethoxyhexane, 1,1,1-triethoxyoctane, 1,1,1-trimethoxyoctane, 1,1,1-triethoxyoct-2-ene, 1,1,1-trimethoxyoct-2-ene, 1,1,1-triethoxyoct-2-yne, 1,1,1-trimethoxyoct-2-yne, 1,1,1,7,7,7-hexaethoxyoctane, 1,1,1,7,7,7-hexamethoxyoctane, 1,1,1,7,7,7-hexaethoxyoct-2-ene, 1,1,1,7,7,7-hexaethoxyoct-2-yne, 6-carboethoxy-1,1,1-triethoxyhexane, and 6-carboethoxy-1,1,1-triethoxyhex-2-ene.

Protected acetal derivatives of amides

N,N-dimethylformamide dimethyl acetal, 1-dimethylamino-1,1-dimethoxyethane, 1-diethylamino-1,1-diethoxyethane, 1-dimethylamino-1,1-dimethoxypropane, 1-dimethylamino-1,1-dimethoxybutane, 1-dimethylamino-1,1-dimethoxypentane, 1-dimethylamino-1,1-dimethoxyhexane, 1-dimethylamino-1,1-dimethoxyoctane, 1-dimethylamino-1,1-dimethoxyoct-2-ene, 1-dimethylamino-1,1-dimethoxyoct-2-yne, 6-carbomethoxy-1-dimethylamino-1,1-dimethoxyhexane, 6-carbomethoxy-1-dimethylamino-1,1-dimethoxyhex-2-ene, 6-carbomethoxy-1-dimethylamino-1,1-dimethoxyhex-2-ene, N,N-diethylformamide dimethyl acetal, 1-pyrrolidyl-1,1-dimethoxyethane, 1-morpholino-1,1-diethoxyhexane, 1-piperidyl-1-dimethoxyhept-6-ene, 1-(methylethylamino)-1,1-dimethoxyheptane, 1-(cyclohexylmethylamino)-1,1-dimethoxyoctane, and 6-carboethoxy-1-dipropylamino-1-dimethoxyhexane.

Preferred protected acetal derivatives of amides are those in which $R^{61}$ and/or $R^{62}$ in the formula

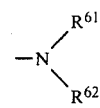

represents a hydrogen atom or an alkyl group having 1 to 10 carbon atoms are preferred.

According to the second reaction of this invention, any of these protected acetal derivatives of organic carbonyl compounds can be reacted with the β-substituted enol cuprate to form the adjacent disubstituted ketone of formula (5)-a.

Specifically, when the protected acetal derivative of an organic carbonyl compound having formula (4)-a is a protected acetal derivative of an aldehyde, ketone or amide, compounds of formula (5)-a are formed in which $R_B$ is a group of the formula

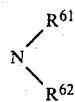

wherein $R^5$ and $R^6$ are as defined above with regard to formula (4)-a, $R^7$ represents a hydrogen atom, an organic group having 1 to 20 carbon atoms, or a group of the formula

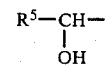

in which $R^{61}$ and $R^{62}$ are as defined hereinabove.

When the protected acetal derivative of the organocarbonyl compound of formula (4)-a is a protected acetal derivative of an ester, compounds of formula (5)-a are formed in which the group $R_B$ is a group of the formula

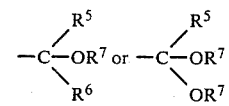

wherein $R^5$ and $R^7$ are as defined hereinabove with respect to formula (4)-a, and $R^6$ is —O—($C_1$–$C_{20}$ organic group), or $R_B$ is a group of the formula

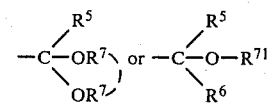

wherein $R^5$ is as defined above with regard to formula (4)-a, $R^6$ is —O—($C_1$–$C_{20}$ organic group), and two $R^7$ groups are linked to each other to form a 5- or 6-membered ring and each $R^7$ is an alkylene group having 2 or 3 carbon atoms participating in the formation of the ring, and $R^{71}$ represents a β- or γ-hydroxyalkyl group formed by the cleavage of the ring.

When the protected acetal derivative of the organic carbonyl group is a protected acetal derivative of an ester, the resulting reaction product mixture is slightly complex in contrast to the case of using the other protected acetal derivatives. It should be understood however that this is irrelevant to the essence of the second reaction in the present invention. When the protected acetal derivative of an ester is used, there are two groups to be split off, and the produce differs depending upon competition between these groups as shown above.

On the other hand, when the second reaction is carried out using the aldehyde of formula (4)-b there are obtained adjacently disubstituted ketones expressed by the following formula (5)-b

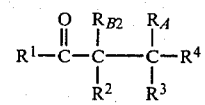

wherein $R^1$, $R^2$, $R^3$, $R^4$ and $R_A$ are as defined hereinabove with respect to formula (1), and $R_{B2}$ is a group of the formula

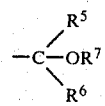

in which $R^5$ is as defined with regard to formula (4)-b.

Examples of the organic group having 1 to 20 carbon atoms for $R^5$ in formula (4)-b are the same as those given hereinabove with regard to formula (1).

Examples of the aldehyde of formula (4)-b are the same as those given hereinabove in exemplifying the protected acetal derivatives of aldehydes.

Investigations of the present inventors have shown that among organic carbonyl compounds (not the protected acetal derivatives), only aldehydes react with the β-substituted enol cuprate in the presence of a Lewis acid as does the protected acetal derivative of an organic carbonyl compound on the basis of the essence of the reactions in accordance with this invention, whereas esters, amides and ketones do not.

Since, however, the reaction of an aldehyde with the β-substituted enol cuprate in the presence of a Lewis acid gives a product which forms an unstable anion, this product is then reacted with a proton donor, and the resulting product is isolated as the α-(α-hydroxyorganic group)substituted, β-substituted adjacently disubstituted ketone of formula (5)-b.

For example, water is preferably used as the proton donor. Usually, water which comes into the reaction system during an operation of isolation and purification readily induces this reaction. Hence, it is not necessary to go so far as to incorporate the reaction of the product with proton donors as a reaction operation.

The second reaction in this invention is performed by using the protected acetal derivative of organic carbonyl compound having of formula (4)-a or the aldehyde of formula (4)-b in an amount of preferably 0.6 to 2 moles, especially 0.9 to 1.2 moles, per mole of the β-substituted enol cuprate.

As is seen from the above description of the first and second reactions, the present invention has the further advantage that the final product can be formed in high yields using nearly equimolar proportions of the reagents, i.e. the α,β-unsaturated dicarbonyl compound, the organolithium compound, the cuprous salt and the protected acetal derivative of an organic carbonyl compound or the aldehyde, throughout the reactions, and that the reaction mixture obtained by the performance of the first reaction can be directly subjected to the second reaction without isolating the resulting β-substituted enol cuprate from it.

After the second reaction is over (the state of progress of the reaction can be traced by, for example, thin-layer chromatography), the reaction mixture is treated by ordinary treating operations to afford the desired adjacently disubstituted ketone.

For example, the final product can be obtained by treating the reaction mixture with water or an aqueous solution of a strong electrolyte such as an ammoniac aqueous solution of ammonium chloride for 0.1 to 1 hour, and then extracting, washing and concentrating it in a customary manner to form a crude product, and purifying the crude product by distillation, chromatography (for example, on $Al_2O_3$), etc.

Investigations of the present inventors have shown that when the process of this invention is carried out using an α,β-unsaturated carbonyl compound of the following formula (1)-a

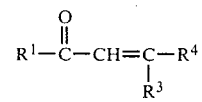

(1)-a wherein $R^1$, $R^3$ and $R^4$ are as defined hereinabove with regard to formula (1), [a compound of formula (1) in which $R^2$ is hydrogen] as the α,β-unsaturated carbonyl compound in the first reaction and the protected acetal derivative of an organic carbonyl compound in the second reaction, the aforesaid known after-treatment of the product after the reaction leads to isolation of the desired adjacently disubstituted ketone in which the substituent at the α-position is bonded to the carbon atom at the α-position through a double bond. This adjacently disubstituted ketone is expressed by the following formula (5)-c

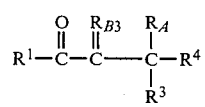

(5)-c wherein $R^1$, $R^3$, $R^4$ and $R_A$ are as defined hereinabove with regard to formula (1), and $R_{B3}$ represents a group derived from the protected acetal derivative of an organic carboxyl group expressed by formula (4)-a, and when $R^6$ in formula (4)-a represents a hydrogen atom, an organic group having 1 to 20 carbon atoms or a group of the formula

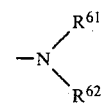

in which $R^{61}$ and $R^{62}$ are as defined above, $R_{B3}$ represents a group of the formula

and when $R^6$ in formula (4)-a represents —O— ($C_1$-$C_{20}$ organic group) and $R^7$ represents an organic group having 1 to 20 carbon atoms, $R_{B3}$ represents a group of the formula

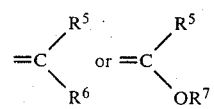

with the proviso that when two $R^7$ groups are linked to each other to form a 5- or 6-membered ring, $R_{B3}$ represents a group of the formula

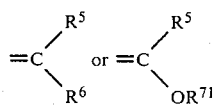

in which $R^{71}$ represents a β- or γ-hydroxyalkyl group.

Examples of the adjacently disubstituted ketones produced by the process of this invention include
3-butyl-2-(1'-hydroxy-1'-phenyl)methylcyclopentanone,
3-butyl-2-hydroxymethylcyclopentanone,
3-butyl-2-hydroxymethylcyclohexanone,
3-butyl-2-(1'-hydroxy-2-propenyl)cyclopentanone,
3-butyl-2-(1'-hydroxy-1'-n-butoxycarbonyl)methylcyclopentanone,
methyl 17,18,19,20-tetranor-9-oxo-9-hydroxyprostanoate,
2-hydroxymethyl-3-(3'-tetrahydropyranyloxy-1-octenyl)-4-tetrahydropyranyloxycyclopentanone,
7-hydroxy-11-deoxyprostaglandin E$_1$ methyl ester,
7-hydroxyprostaglandin E$_1$ methyl ester tetrahydropyranyl ether,
2-dimethoxymethyl-3-(3'-t-butyldimethylsiloxy-1-octenyl)cyclopentanone, and
2-(α-ethoxyethylene)-3-butylcyclopentanone.

Some of the adjacently disubstituted ketones obtained by the process of this invention, as shown in Examples given hereinbelow, are prostaglandins which are expected to have biological activities as medicines, and others are useful compounds which will find wide applications as intermediates for the synthesis of medicines, agricultural chemicals and perfumes. For example, β-substituted-α-hydroxymethyl-ketones obtained by the reaction of formaldehyde can be converted to α-methylene-ketones by dehydration reaction which are useful as drugs expected to have anticancerous activity and antimicrobial activity. These α-methylene-ketones can be converted to the aforesaid prostaglandins and their analogs by known methods.

As is seen from the above-exemplified adjacently disubstituted ketones, the process of this invention gives prostaglandin analogs when using a compound of the following formula (1)-b

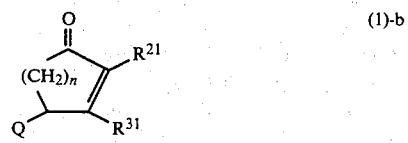

wherein $R^{21}$ and $R^{31}$ are identical or different and represent a hydrogen atom or an alkyl group having 1 to 4 carbon atoms, Q represents a hydrogen atom or a protected hydroxyl group, and n is an integer of 1 or 2,
or a cyclopentenone corresponding to formula (1)-b in which $R^{21}$ represents a hydrogen atom [formula (1)-c] and n is 1 is used as the α,β-unsaturated carbonyl compound. Such a process of this invention is simpler and more efficient than any of convetional processes known to produce prostaglandin analogs.

Accordingly, the process of this invention provides novel prostaglandin analogs with industrial advantage. Thus, the present invention also provides a pharmaceutical composition comprising such a novel prostaglandin analog as an active ingredient.

The novel prostaglandin analogs provided by the present invention are 7-hydroxyprostaglandins E$_1$, the stereoisomers thereof, or the protected derivatives thereof having the following formula (5)-c-1

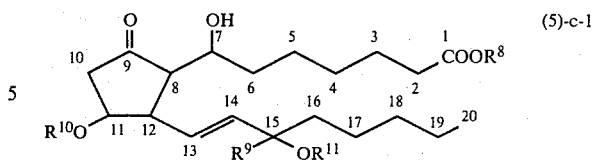

wherein $R^8$ represents a hydrogen atom, a methyl group or an ethyl group, $R^9$ represents a hydrogen atom or a methyl group, and $R^{10}$ and $R^{11}$ are identical or different, and each represents a hydrogen atom, a tetrahydropyranyl group or a t-butyldimethylsilyl group.

The compounds expressed by formula (5)-c-1 embrace compounds of the formulae

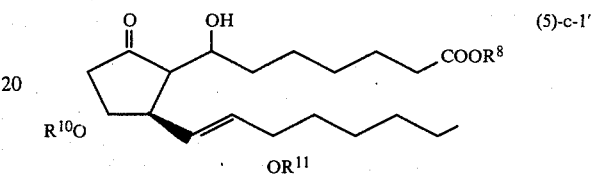

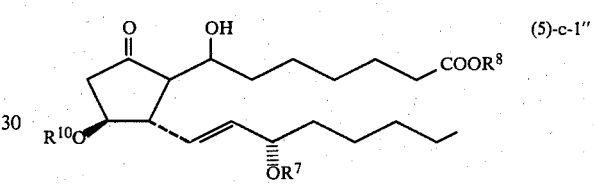

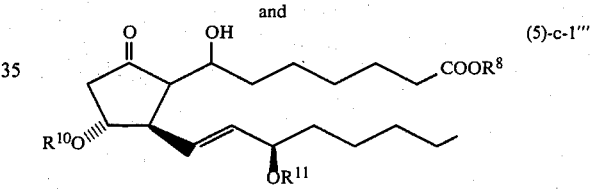

either singly or as mixtures in arbitrary ratios ($R^8$, $R^{10}$ and $R^{11}$ in the three formulae are as defined in with respect to formula (5)-c-1 above).

Among the compounds of formula (5)-c-1 provided by this invention, 7-hydroxyprostaglandin E$_1$ or the stereoisomers thereof having the following formula (A)

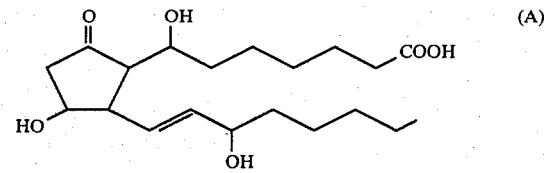

can be produced by subjecting the 7-hydroxyprostaglandin E$_1$ or its stereoisomer corresponding to formula (5)-c-1 in which $R^8$, $R^{10}$ and $R^{11}$ are protected by groups other than hydrogen and obtained by the process of this invention in which the second reaction is performed using an aldehyde, to a known procedure, for example, hydrolysis under acidic or alkaline conditions, or microbial hydrolysis.

Investigations of the present inventors have led to the discovery that the 7-hydroxyprostaglandin E$_1$ or its stereoisomers of formula (A) have superior anti-thrombotic activity and anti-ulcer activity.

Accordingly, the present invention further provides an anti-thrombotic composition comprising a pharmaceutically effective amount of the 7-hydroxyprostaglandin $E_1$ or its stereoisomer of formula (A) and a pharmaceutically acceptable carrier.

These compounds can be administered to mammals including man when it is desired to inhibit platelet aggregation and to inhibit or prevent thrombus formation. Thus, these compounds are useful for various prophylactic and therapeutic purposes such as the prevention of cardiovascular infarctions and post-operative thrombosis, the promotion of patency of vascular prostheses after surgical operation, and the prevention and treatment of atherosclerosis, arteriosclerosis, etc.

They are also used to prevent onset of cerebral ischemia in patients of senile diseases, and to prevent or treat myocardial infarction and poplexy for a long period of time after their seizure.

For these purposes, the compounds of this invention can be administered perorally, intrarectally, or parenterally (e.g., intravenously, subcutaneously, intramuscularly). Preferably, they are administered parenterally.

For peroral administration, the compounds of the invention are formulated into solid or liquid preparations. Solid preparations include tablets, pills, powders and granules. In such solid preparations, at least one active compound is mixed with at least one inert diluent such as calcium carbonate, potato starch, alginic acid or lactose. Other additives such as lubricants (e.g., magnesium stearate) may also be included. Drug formulation is performed in a customary manner.

Liquid preparations for oral administration include emulsions, solutions, suspensions, syrups and elixirs and a general pharmaceutically acceptable inert diluent such as water or liquid paraffin. In addition to the inert diluent, these pharmaceutical preparations contain auxiliary agents such as wetting agents, suspending aids, sweetenings, flavoring agents, perfumes or antiseptics.

The liquid preparations may be encapsulated in absorbable materials such as gelatin.

Solid preparations for intrarectal administration include suppositories containing at least one active compound and prepared by a method known per se.

Preparations for parenteral administration are aseptic aqueous or non-aqueous solutions, suspensions or emulsions. Non-aqueous solutions or suspensions contain propylene glycol, polyethylene glycol, vegetable oils such as olive oil, and injectable organic esters such as ethyl oleate, etc. These preparations can also include auxiliary agents such as antiseptics, wetting agents, emulsifiers and dispersing agents. These preparations can be sterilized, for example, by filtration through a bacterium-holding filter, mixing of a bactericide, or by irradiation. Alternatively, aseptic solid preparations are first produced, and immediately prior to use, dissolved in aseptic water or an aseptic solvent for injection.

The dosage of the 7-hydroxyprostaglandin $E_1$ or its stereoisomer, an active compound in accordance with this invention, is about 0.1 μg to about 100 mg, preferably about 1 μg to about 10 mg, per day per kilogram of body weight. Of course, the dosage depends upon the condition, body weight and age of a patient and the route of administration.

According to this invention, there is also provided an anti-thrombotic composition containing the 7-hydroxyprostaglandin $E_1$ or its stereoisomer of formula (A) as an inclusion compound of cyclohextrin. By converting this active compound into an inclusion compound of cyclodextrin, the stability of the 7-hydroxyprostaglandin or its stereoisomer increases to make it suitable for oral administration.

This inclusion compound can be prepared by dissolving cyclodextrin in water and/or a water-miscible organic solvent, and adding the solution to a solution of the 7-hydroxyprostaglandin compound in a water-miscible organic solvent. The mixture is warmed, and the desired cyclodextrin inclusion compound can be isolated by concentration under reduced pressure. Or the mixture is cooled, and the desired product is isolated by filtration or decantation. The ratio of the organic solvent to water varies depending upon the solubilities of the starting materials and the product. Preferably, during the production of the cyclodextrin inclusion compound, the temperature should not exceed 70° C. $\alpha$-, $\beta$-, and $\gamma$-cycldextrins or mixtures thereof are used in the production of the cyclodextrin inclusion compound.

The following Examples illustrate the present invention in more detail.

EXAMPLE 1

Synthesis of 3-n-butyl-2-(hydroxymethyl) cyclopentanone (No. 100)

Cuprous iodide (325 mg; 1.7 mmoles) was weighed into a 100 ml flask, and the inside atmosphere of the flask was purged with argon. Anhydrous ether (20 ml) was added, and then, 687 mg (3.4 mmoles, 0.85 ml) of tri-n-butylphosphine was added at room temperature. The mixture was stirred for 10 minutes. Then, the mixture was cooled to $-78°$ C., and 0.91 ml (1.7 mmoles) of n-butyllithium (1.86 M hexane solution) was slowly added dropwise. The mixture was stirred at $-78°$ C. for 30 minutes, and 194 mg (1.7 mmoles) of a boron trifluoride-ether complex was added, followed by stirring for 5 minutes. Thereafter, a solution of 123 mg (1.5 mmoles) of 2-cyclopentenone in 5 ml of anhydrous ether was slowly added dropwise, and the mixture was stirred at $-78°$ C. for 10 minutes, at $-55°$ C. for 20 minutes and then at $-40°$ C. for 10 minutes. Anhydrous tetrahydrofuran (20 ml) was added, and 120 mg (4 mmoles) of formaldehyde was blown into the mixture under a stream of argon. The temperature of the mixture was gradually raised to room temperature, and the product was hydrolyzed with a saturated aqueous solution of ammonium chloride and then extracted with ether. The organic layer was dried over anhydrous sodium sulfate, and concentrated under reduced pressure by an evaporator. The crude product was subjected to silica gel column chromatography (15 g of ammonia-treated silica gel; benzene/ethyl acetate=5/1 as an eluent) to afford 217 mg (yield 85%) of the captioned compound.

The properties of this product were as follows:

Rf(benzene/ethyl acetate=1/1 as a developing solvent): 0.40.

IR (liquid film): 3400 cm$^{-1}$ (OH), 1730 cm$^{-1}$ (C=O).

NMR (CCl$_4$) $\delta$: 0.8–1.1 (m, 3H, CH$_3$), 1.1–2.4 (m, 12H, CH$_2$ and CH), 2.92 (br.s, 1 H, OH), 3.4–3.9 (m, 2H, CH$_2$OH).

EXAMPLE 2

Synthesis of 3-n-butyl-2-(phenylhydroxymethyl)cyclopentenone (No. 102)

Cuprous iodide (325 mg; 1.7 mmoles) was weighed into a 50 ml flask, and the inside atmosphere of the flask was purged with argon. Anhydrous ether (20 ml) was added, and then 687 mg (3.4 mmoles; 0.85 ml) of tri-n-butylphosphine was added at room temperature. The mixture was stirred for 10 minutes. It was then cooled to −78° C., and 1.14 ml (1.7 mmoles) of n-butyllithium (as a 1.49 M hexane solution) was slowly added dropwise. The mixture was stirred at −78° C. for 15 minutes, and 194 mg (1.7 mmoles) of a boron trifluoride-ether complex was added, followed by stirring for 5 minutes. Then, a solution of 123 mg (1.5 mmoles) of 2-cyclopentenone in 5 ml of anhydrous ether was slowly added dropwise. The mixture was stirred at −78° C. for 10 minutes, at −55° C. for 30 minutes, and then at −40° C. for 20 minutes. Anhydrous tetrahydrofuran (5 ml) was added, and then a solution of 212 mg (2 mmoles) of benzaldehyde in 10 ml of anhydrous tetrahydrofuran was added. The temperature of the mixture was gradually raised to room temperature, and the product was hydrolyzed with a saturated aqueous solution of ammonium chloride, and extracted with ether. The organic layer was dried over anhydrous sodium sulfate, and concentrated under reduced pressure by an evaporator. The crude product was subjected to silica gel column chromatography (10 g of ammonia-treated silica gel; benzene as an eluent) to afford 306 mg (yield 83%, a mixture of stereoisomers having different polarities) of the captioned compound.

The properties of the product were as follows:
Compound with lower polarity (No. 102')
Rf(benzene/ethyl acetate=8/1 as a developing solvent): 0.43.
IR (liquid film): 3440 cm$^{-1}$(OH), 1735 cm$^{-1}$(C=O).
NMR (CCl$_4$) δ: 0.6–1.5 (m, 12H, CH$_3$, CH$_2$ and CH), 1.9–2.4 (m, 3H, α-position CH$_2$ and CH), 3.53 (br.s, 1H, OH), 4.71 (d, J=7 Hz, 1H, CHOH), 7.24 (S, 5H, C$_6$H$_5$).
Mass (m/e): 246 (M+), 228 (M+−18).
Compound with higher polarity (No. 102")
Rf(benzene/ethyl acetate=8/1 as a developing solvent): 0.35.
IR (liquid film): 3400 cm$^{-1}$(OH), 1735 cm$^{-1}$(C=O).
NMR (CCl$_4$) δ: 0.6–2.6 (m, 15H, CH$_3$, CH$_2$ and CH), 4.43 (br.s, 1H, OH), 5.16 (d, J=3 Hz, 1H, CHOH), 7.24 (m, 5H, C$_6$H$_5$).
Mass (m/e): 246 (M+), 228 (M+−18).

EXAMPLE 3

Synthesis of 3-n-butyl-2-(1-hydroxy-n-butyl)cyclopentanone (No. 104)

The same procedure as in Example 2 was repeated using 144 mg (2 mmoles) of 1-butanal. There was obtained 270 mg (yield 85%; a mixture of stereo-isomers having different polarities) of the captioned compound.

The properties of the product were as follows:
Compound having lower polarity (No. 104')
Rf(benzene/ethyl acetate=20/1 as a developing solvent): 0.39.
IR (liquid film): 3400 cm$^{-1}$(OH), 1740 cm$^{-1}$(C=O).
NMR (CCl$_4$)δ: 0.8–1.1 (m, 6H, CH$_3$), 1.2–2.0 (m, 13H, CH$_2$ and CH), 2.0–2.4 (m, 4H, α-position CH$_2$, CH and OH), 3.3–3.7 (m, 1H, CHOH).
Mass (m/e): 212 (M+), 194 (M+−18).
Compound having higher polarity (No. 104")
Rf(benzene/ethyl acetate=20/1 as a developing solvent): 0.34.
IR(liquid film): 3410 cm$^{-1}$(OH), 1730 cm$^{-1}$(C=O).

NMR(CCl$_4$)δ: 0.8–1.1 (m, 6H, CH$_3$), 1.2–2.4 (m, 16H, CH$_2$ and CH), 2.53 (s, 1H, OH), 3.7–3.9 (m, 1H, CHOH).
Mass (m/e): 212 (M+), 994 (M+−18).

EXAMPLE 4

Synthesis of 3-n-butyl-2-(1-hydroxy-2-propenyl)cyclopentanone (No. 106)

The same procedure as in Example 2 was performed using 112 mg (2 mmoles) of acrolein. There was obtained 205 mg (yield 70% of the captioned compound.

The properties of the product were as follows:
Rf(benzene/ethyl acetate=10/1 as a developing solvent): 0.25.
IR(liquid film): 3440 cm$^{-1}$(OH), 1740 cm$^{-1}$(C=O), 990 cm$^{-1}$ and 920 cm$^{-1}$(CH=CH$_2$).
NMR(CCl$_4$) δ: 0.8–1.1 (m, 3H, CH$_3$), 1.1–2.4 (m, 12H, CH$_2$ and CH), 2.7–2.9 (m, 1 H, OH), 4.1–4.5 (m, 1H, CHOH), 5.0–5.4 (m, 2H, CH=CH$_2$), 5.6–6.1 (m, 1H, CH=CH$_2$).

EXAMPLE 5

Synthesis of 3-n-butyl-2-(3-phenyl-1-hydroxy-2-propenyl)cyclopentanone (No. 108)

The same procedure as in Example 2 was repeated using 264 mg (2 mmoles) of cinnmaldehyde. There was obtained 371 mg (yield 91%) of the captioned compound.

The properties of the product were as follows:
Rf(benzene/ethyl acetate=8/1 as a developing solvent): 0.33.
IR(liquid film): 3380 cm$^{-1}$(OH), 1730 cm$^{-1}$(C=O), 965 cm$^{-1}$(C=C).
NMR(CCl$_4$) δ: 0.8–1.1 (m, 3H, CH$_3$), 1.2–2.4 (m, 12H, CH$_2$ and CH), 3.14 (br.s, 1H, OH), 4.3–4.8 (m, 1H, CHOH), 6.1–6.7 (m, 2H, CH=CH), 7.25 (br.s, 5H, C$_6$H$_5$).

EXAMPLE 6

Synthesis of 3-n-butyl-2-(1-hydroxy-2-keto-3-oxaheptyl)cyclopentanone (No. 110)

The same procedure as in Example 2 was repeated using 260 mg (2 mmoles) of n-butylglyoxalate. There was obtained 115 mg (yield 28%) of the captioned compound.

The properties of the product were as follows:
Rf(benzene/ethyl acetate=10/1 as a developing solvent): 0.29.
IR(liquid film): 3440 cm$^{-1}$(OH), 1735 cm$^{-1}$(C=O).
NMR(CCl$_4$) δ: 0.8–1.1 (m, 6H, CH$_3$), 1.1–2.5 (m, 16H, CH$_2$ and CH), 3.9–4.3 (m, 3H, CHOH and OCH$_2$CH$_2$).
Mass(m/e): 270 (M+), 252 (M+−18).

EXAMPLE 7

Synthesis of 3-n-butyl-2-(1-hydroxy-7-keto-8-oxanonyl)cyclopentanone (No. 112)

The same procedure as in Example 2 was repeated using 316 mg (2 mmoles) of methyl 7-ketoheptanoate. There was obtained 285 mg (yield 79%) of the captioned compound.

The properties of the product were as follows:

Rf(benzene/ethyl acetate=8/1 as a developing solvent): 0.12.

IR(liquid film): 3460 cm$^{-1}$ (OH), 1735 cm$^{-1}$ (C=O).
NMR(CCl$_4$) δ: 0.8–1.1 (m, 3H, CH$_3$), 1.1–1.9 (m, 17H, CH$_2$ and CH), 1.9–2.3 (m, 5H, α-position CH$_2$ and CH), 2.5–2.7 (m, 1H, OH), 3.5–3.8 (m, 1H, CHOH), 3.58 (S, 3H, OCH$_3$).

EXAMPLE 8

Synthesis of 2-(hydroxymethyl)-3-[3-(tetrahydropyran-2-yloxy)-1-trans-octenyl]cyclopentanone (No. 114)

Cuprous iodide (325 mg; 1.7 mmoles) was weighed into a 100 ml flask, and the inside atmosphere of the flask was purged with argon. Anhydrous ether (10 ml) was added, and then 687 mg (3.4 mmoles; 0.85 ml) of tri-n-butylphosphine was added at room temperature. The mixture was stirred for 10 minutes. The mixture was then cooled to −78° C., and a solution of 1.7 mmoles of 1-lithio-3-(tetrahydropyran-2-yloxy)-1-trans-octene in a mixture of 10 ml of diethyl ether and 2 ml of pentane was added. The mixture was stirred at −78° C. for 30 minutes, and a solution of 123 mg (1.5 mmoles) of 2-cyclopentenone in 5 ml of anhydrous ether was slowly added dropwise. The mixture was stirred at −78° C. for 10 minutes, and 194 mg (1.7 mmoles) of a boron trifluoride-ether complex was added. The mixture was stirred at −78° C. for 10 minutes, at −55° C. for 20 minutes, and then at −40° C. for 10 minutes. Then, 25 ml of anhydrous tetrahydrofuran was added, and 120 mg (4 mmoles) of formaldehyde was blown into the mixture in a stream of argon. The temperature of the mixture was raised gradually to room temperature, and the mixture was hydrolyzed with a saturated aqueous solution of ammonium chloride and extracted with ether. The organic layer was dried over anhydrous sodium sulfate, and concentrated under reduced pressure by an evaporator. The crude product was subjected to silica gel column chromatography (15 g of ammonia-treated silica gel; benzene/ethyl acetate=1:1 as an eluent) to afford 231 mg (yield 47%) of the captioned compound.

The product properties of the product were as follows:

Rf(benzene/ethyl acetate=1/1 as a developing solvent): 0.32.

IR(liquid film): 3420 cm$^{-1}$ (OH), 1735 cm$^{-1}$ (C=O).
NMR(CCl$_4$) δ: 0.8–1.1 (m, 3H, CH$_3$), 1.2–2.9 (m, 21H, CH$_2$, CH and OH), 3.2–4.1 (m, 5H, OCH$_2$CH$_2$, CH$_2$OH and CHOTHP), 4.5–4.7 (m, 1H, OCHO), 6.3–6.8 (m, 2H, CH=CH).

EXAMPLE 9

Synthesis of 2-(hydroxymethyl)-3-[3-(tetrahydropyran-2-yloxy)-1-trans-octenyl]-4-(tetrahydropyran-2-yloxy)cyclopentanone (No. 116)

Cuprous iodide (325 mg; 1.7 mmoles) was weighed into a 100 ml flask, and the inside atmosphere of the flask was purged with argon. Anhydrous ether (10 ml) was added, and then 687 mg (3.4 mmoles; 0.85 ml) of tri-n-butylphosphine was added at room temperature. The mixture was stirred for 10 minutes. It was then cooled to −78° C., and a solution of 1.7 mmoles of 1-lithio-3-(tetrahydropyran-2-yloxy)-1-trans-octene in a mixture of 10 ml of diethyl ether and 2 ml of pentane was added. The mixture was stirred at −78° C. for 30 minutes, and then a solution of 273 mg (1.5 mmoles) of 4-(tetrahydropyran-2-yloxy)-2-cyclopentenone in 5 ml of anhydrous ether was slowly added dropwise. The mixture was stirred at −78° C. for 10 minutes. Then, 194 mg (1.7 mmoles) of a boron trifluoride-ether complex was added, and the mixture was stirred at −78° C. for 10 minutes, at −55° C. for 20 minutes and then at −40° C. for 10 minutes. Anhydrous tetrahydrofuran (25 ml) was added, and 120 mg (4 mmoles) of formaldehyde was blown into the mixture in a stream of argon. The temperature of the mixture was gradually raised to room temperature, and the product was hydrolyzed with a saturated aqueous solution of ammonium chloride and extracted with ether. The organic layer was dried over anhydrous sodium sulfate, and concentrated under reduced pressure. The crude product was subjected to silica gel column chromatography (15 g of ammonia-treated silica gel; benzene/ethyl acetate=5/1 as an eluent) to afford 324 mg (yield 52%) of the captioned compound.

The properties of the product were as follows:

Rf(benzene/ethyl acetate=1/1 as a developing solvent): 0.31, 0.26.

IR(liquid film): 3440 cm$^{-1}$(OH), 1740 cm$^{-1}$(C=O).
NMR(CDCl$_3$) δ: 0.8–1.0 (m, 3H, CH$_3$), 1.2–3.0 (m, 25H, CH$_2$, CH and OH), 3.3–4.3 (m, 8H, OCH$_2$CH$_2$, CHOTHP and CH$_2$OH), 4.6–4.8 (m, 2H, OCHO), 5.4–5.8 (m, 2H, CH=CH).

EXAMPLE 10

Synthesis of 2-(1-hydroxy-7-keto-8-oxanonyl)-3-[3-(tetrahydropyran-2-yloxy)-1-trans-octenyl]cyclopentanone (No. 118)

Cuprous iodide (325 mg; 1.7 mmoles) was weighed into a 50 ml flask, and the inside atmosphere of the flask was purged with argon. Anhydrous ether (10 ml) was added, and then 687 mg (3.4 mmoles; 0.85 ml) of tri-n-butylphosphine was added at room temperature. The mixture was stirred for 10 minutes. It was then cooled to −78° C., and a solution of 1.7 mmoles of 1-lithio-3-(tetrahydropyran-2-yloxy)-1-trans-octene in a mixture of 10 ml of diethyl ether and 2 ml of pentane was added. The mixture was stirred at −78° C. for 30 minutes. A solution of 123 mg (1.5 mmoles) of 2-cyclopentenone in 5 ml of anhydrous ether was slowly added dropwise. The mixture was stirred for 10 minutes at −78° C., and then 194 mg (1.7 mmoles) of a boron trifluoride-ether complex was added. The mixture was stirred at −78° C. for 10 minutes, at −55° C. for 20 minutes, and then at −40° C. for 10 minutes. Then, 5 ml of anhydrous tetrahydrofuran was added and a solution of 316 mg (2 mmoles) of methyl 7-ketoheptanoate in 10 ml of anhydrous tetrahydrofuran was added. The temperature of the mixture was gradually raised to room temperature. The product was hydrolyzed with a saturated aqueous solution of ammonium chloride and extracted with ether. The organic layer was dried over anhydrous sodium sulfate, and concentrated under reduced pressure by an evaporator. The crude product was subjected to silica gel column chromatography (15 g of ammonia-treated silica gel; benzene/ethyl acetate=3/1 as an eluent) to afford 322 mg (yield 47%) of the captioned compound.

The properties of the product were as follows:

Rf(benzene/ethyl acetate=1/1 as a developing solvent): 0.40.

NMR(CCl$_4$) δ: 0.8–1.1 (m, 3H, CH$_3$), 1.2–2.9 (m, 31H, CH$_2$, CH and OH), 3.2–4.1 (m, 4H, OCH$_2$CH$_2$, CHOTHP and CHOH), 3.60 (s, 3H, OCH$_3$), 4.5–4.7 (m, 1H, OCHO), 5.3–5.8 (m, 2H, CH=CH).

EXAMPLE 11

Synthesis of 2-(1-hydroxy-7-keto-8-oxanonyl)-3-[3-(tetrahydropyran-2-yloxy)-1-trans-octenyl]-4-(tetrahydropyran-2-yloxy)cyclopentanone (No. 120)

The same procedure as in Example 10 was repeated using 273 mg (1.5 mmoles) of 4-(tetrahydropyran-2-yloxy)-2-cyclopentenone instead of the 2-cyclopentenone. Thus, 423 mg (yield 53%) of the captioned compound was obtained.

The properties of the product were as follows:

Rf(benzene/ethyl acetate=1/1 as a developing solvent): 0.43.

IR(liquid film): 3440 cm$^{-1}$(OH), 1740 cm$^{-1}$(C=O).

NMR(CCl$_4$) δ: 0.8–1.1 (m, 3H, CH$_3$), 1.1–2.8 (m, 35H, CH$_2$, CH and OH), 3.2–4.2 (m, 7H, OCH$_2$CH$_2$, CHOTHP and CHOH), 3.62 (s, 3H, OCH$_3$), 4.4–4.8 (m, 2H, OCHO), 5.4–5.8 (m, 2H, CH=CH).

Treatment of this product in a tetrahydrofuran solvent in a customary manner afforded 2-(1-hydroxy-7-keto-8-oxanonyl)-3-(3-hydroxy-1-trans-octenyl)-4-hydroxycyclopentanone (dl-7-OHPGE$_1$ methyl ester) (No. 122).

EXAMPLE 12

Synthesis of 3-n-butyl-2-(dimethoxymethyl)cyclopentanone (No. 124)

Cuprous iodide (325 mg; 1.7 mmoles) was weighed into a 50 ml flask, and the inside atmosphere of the flask was purged with argon. Anhydrous ether (20 ml) was added, and then 687 mg (3.4 mmoles; 0.85 ml) of tri-n-butylphosphine was added at room temperature. The mixture was stirred for 10 minutes. Then, it was cooled to −78° C., and 0.91 ml (1.7 mmoles) of n-butyllithium (as 1.86 M hexane solution) was slowly added dropwise. The mixture was stirred at −78° C. for 30 minutes, and 194 mg (1.7 mmoles) of a boron trifluoride/ether complex was added, followed by stirring for 10 minutes. Then, a solution of 123 mg (1.5 mmoles) of 2-cyclopentenone in 5 ml of anhydrous ether was slowly added dropwise. The mixture was stirred at −78° C. for 10 minutes, at −55° C. for 20 minutes, and then at −40° C. for 10 minutes. Then, 5 ml of anhydrous tetrahydrofuran was added, and a solution of 212 mg (2 mmoles) of methyl ortho-formate in 10 ml of anhydrous tetrahydrofuran was added. The temperature of the mixture was raised gradually to room temperature, and the product was hydrolyzed with a saturated aqueous solution of ammonium chloride, and extraceted with ether. The organic layer was dried over anhydrous sodium sulfate, and concentrated under reduced pressure by an evaporator. The crude product was subjected to silica gel column chromatography (10 g of ammonia-treated silica gel; benzene/ethyl acetate=20/1 as an eluent) to afford 277 mg (yield 86%) of the captioned compound.

The properties of the product were as follows:

Rf(benzene/ethyl acetate 8/1 as a developing solvent): 0.46.

IR(liquid film): 1740 cm$^{-1}$(C=O).

NMR(CCl$_4$) δ: 0.8–1.1 (m, 3H, CH$_3$), 1.1–2.4 (m, 12H, CH$_2$ and CH), 3.38 (s, 6H, OCH$_3$), 4.48 (d, J=3 Hz, 1H, CH(OCH$_3$)$_2$).

EXAMPLE 13

Synthesis of 2-(dimethoxymethyl)-3-[3-(tetrahydropyran-2-yloxy)-1-trans-octenyl]cyclopentanone (No. 126)

Cuprous iodide (325 mg; 1.7 mmoles) was weighed into a 50 ml flask, and the inside atmosphere of the flask was purged with argon. Anhydrous ether (10 ml) was added, and then 687 mg (3.4 mmoles; 0.85 ml) of tri-n-butylphosphine was added at room temperature. The mixture was stirred for 10 minutes. It was then cooled to −78° C. and 1.7 mmoles of 1-lithio-3-(tetrahydropyran-2-yloxy)-1-trans-octene was added. The mixture was stirred at −78° C. for 30 minutes, and a solution of 123 mg (1.5 mmoles) of 2-cyclopentenone in 5 ml of anhydrous ether was slowly added dropwise. The mixture was stirred at −78° C. for 10 minutes, and 194 mg (1.7 mmoles) of a boron trifluoride-ether complex was added. The mixture was stirred at −78° C. for 10 minutes, at −55° C. for 20 minutes, and then at −40° C. for 10 minutes. Anhydrous tetrahydrofuran (5 ml) was added and then a solution of 212 mg (2 mmoles) in 10 ml of anhydrous tetrahydrofuran was added. The temperature of the mixture was raised gradually to room temperature, and the product was hydrolyzed with a saturated aqueous solution of ammonium chloride and extracted with ether. The organic layer was dried over anhydrous sodium sulfate, and concentrated under reduced pressure by an evaporator. The crude product was subjected to silica gel column chromatography (15 g of ammonia-treated silica gel; benzene/ethyl acetate=10/1) to afford 169 mg (yield 30%) of the captioned compound.

The properties of the product were as follows:

Rf(benzene/ethyl acetate=5/1 as a developing solvent): 0.25.

IR(liquid film): 1740 cm$^{-1}$(C=O).

NMR(CCl$_4$) δ: 0.8–1.1 (m, 3H, CH$_3$), 1.2–2.8 (m, 20H, CH$_2$ and CH), 3.1–4.2 (m, 3H, OCH$_2$CH$_2$ and CHOTHP), 3.34 and 3.37 (s, 6H, OCH$_3$), 4.4–4.8 (m, 2H, CH(OCH$_3$)$_2$ and CHOTHP), 5.2–5.8 (m, 2H, CH=CH).

EXAMPLE 14

Synthesis of 2-(dimethoxymethyl)-3-[3-(tetrahydropyran-2-yloxy)-1-trans-octenyl]-4-(tetrahydropyran-2-yloxy)cyclopentanone (No. 128)

The same procedure as in Example 13 was repeated except that 273 mg (1.5 mmoles) of 4-(tetrahydropyran-2-yloxy)-2-cyclopentenone was used instead of the 2-cyclopentenone. Thus, 165 mg (yield 24%) of the captioned compound was obtained.

The properties of the product were as follows:

Rf(benzene/ethyl acetate=2/1 as a developing solvent): 0.51.

IR(liquid film): 1740 cm$^{-1}$(C=O).

NMR(CCl$_4$) δ: 0.8–1.0 (m, 3H, CH$_3$), 1.2–2.8 (m, 24H, CH$_2$ and CH), 3.30 and 3.38 (s, 6H, OCH$_3$), 3.3–4.2 (m, 6H, OCH$_2$CH$_2$ and CHOTHP), 4.5–4.8 (m, 3H, CH(OCH$_3$)$_2$ and OCHO), 5.2–5.7 (m, 2H, CH=CH).

EXAMPLE 15

Synthesis of 3-n-butyl-2-(1-ethoxyethylidene)cyclopentanone (No. 130)

Cuprous iodide (325 mg; 1.7 mmoles) was weighed into a 50 ml flask, and the inside atmosphere of the flask was purged with argon. Anhydrous ether (20 ml) was added, and then 687 mg (3.4 mmoles; 0.85 ml) of tri-n-butylphosphine was added at room temperature. The mixture was stirred for 10 minutes. It was then cooled to −78° C., and 0.91 ml (1.7 mmoles) of n-butyllithium (as a 1.86 M hexane solution) was slowly added dropwise. The mixture was stirred at −78° C. for 30 minutes, and then 194 mg (1.7 mmoles) of a boron trifluoride-ether complex was added, followed by stirring for 5 minutes. A solution of 123 mg (1.5 mmoles) of 2-cyclopentenone in 5 ml of anhydrous ether was slowly added dropwise. The mixture was stirred at −78° C. for 10 minutes, at −55° C. for 20 minutes, and then at −40° C. for 10 minutes. Then, 5 ml of anhydrous tetrahydrofuran was added, and a solution of 324 mg (2 mmoles of triethyl ortho-acetate in 10 ml of anhydrous tetrahydrofuran was added. The temperature of the mixture was raised gradually to room temperature, and the product was hydrolyzed with a saturated aqueous solution of ammonium chloride, and extracted with ether. The organic layer was dried over anhydrous sodium sulfate, and concentrated under reduced pressure by an evaporator. The crude product was subjected to silica gel column chromatography (10 g of ammonia-treated silica gel; benzene/ethyl acetate=10/1 as an eluent). The eluates were further subjected to silica gel column chromatography (ammonia-treated silica gel; benzene/ethyl acetate=20/1 as an eluent) to afford 190 mg (yield 60%) of the captioned compound.

The properties of the product were as follows:

Rf(benzene/ethyl acetate=20/1 as a developing solvent): 0.27.

IR(liquid film): 1690 cm$^{-1}$(C=O), 1600 cm$^{-1}$(C=C).

NMR(CCl$_4$) δ: 0.8–1.1 (m, 3H, CH$_3$), 1.1–2.3 (m, 10H, CH$_2$ and CH), 1.32 (t, J=8 Hz, 3H, OCH$_2$CH$_3$), 2.40 (s, 3H, C=C CH$_3$), 2.8–3.1 (m, 1H, allylic CH), 4.03 (q, J=8 Hz, 2H, OCH$_2$CH$_3$).

EXAMPLE 16

Synthesis of 3-n-butyl-2-(N,N-dimethylaminomethylene)cyclopentanone (No. 132)

The same procedure as in Example 15 was repeated except that 338 mg (2 mmoles) of N,N-dimethylformamide dimethyl acetal was used instead of the triethyl ortho-acetate. Thus, 168 mg (yield 58%) of the captioned compound was obtained.

The properties of the product were as follows:

Rf(alumina, ethyl acetate as a developing solvent): 0.34.

IR(liquid film): 1680 cm$^{-1}$(C=O), 1590 cm$^{-1}$(C=C).

NMR(CCl$_4$) δ: 0.8–1.1 (m, 3H, CH$_3$), 1.1–2.3 (m, 10H, CH$_2$ and CH), 2.9–3.2 (m, 1H, allylic CH), 3.05 (s, 6H, N(CH$_3$)$_2$), 6.90 (br. s, 1H, C=CH-N).

EXAMPLE 17

Synthesis of 2-(N,N-dimethylaminomethylene)-3-[3-(tetrahydropyran-2-yloxy)-1-trans-octenyl]cyclopentanone (No. 134)

Cuprous iodide (325 mg; 1.7 mmoles) was weighed into a 50 ml flask, and the inside atmosphere of the flask was purged with argon. Anhydrous ether (10 ml) was added, the then 687 mg (3.4 mmoles; 0.85 ml) of tri-n-butylphosphine was added at room temperature, followed by stirring for 10 minutes. The mixture was then cooled to −78° C., and 1.7 mmoles of 1-lithio-3-(tetrahydropyran-2-yloxy)-1-trans-octene was added. The mixture was stirred at −78° C. for 30 minutes, and a solution of 123 mg (1.5 mmoles) of 2-cyclopentenone in 5 ml of anhydrous ether was slowly added dropwise. The mixture was stirred at −78° C. for 10 minutes, and 194 mg (1.7 mmoles) of a boron trifluoride-ether complex was added. The mixture was stirred at −78° C. for 10 minutes, at −55° C. for 20 minutes, and then at −40° C. for 10 minutes. Then, 5 ml of anhydrous tetrahydrofuran was added, and then a solution of 338 mg (2 mmoles) of N,N-dimethylformamide dimethyl acetal in 10 ml of anhydrous tetrahydrofuran was added. The temperature of the mixture was gradually raised to room temperature, and the product was hydrolyzed with a saturated aqueous solution of ammonium chloride and extracted with ether. The organic layer was dried over anhydrous sodium sulfate, and concentrated under reduced pressure by an evaporator. The crude product was subjected to alumina column chromatography (neutral activity I, 15 g; benzene/ethyl acetate=1/1 as an eluent) to afford 157 mg (yield 31%) of the captioned compound.

The properties of the product were as follows:

Rf (alumina; benzene/ethyl acetate=1/1 as a developing solvent): 0.30.

NMR(CCl$_4$) δ: 0.8–1.1 (m, 3H, CH$_3$), 1.2–2.7 (m, 19H, CH$_2$ and CH), 3.04 (s, 6H, NCH$_3$), 3.2–4.2 (m, 3H, OCH$_2$CH$_2$ and CHOTHP), 4.4–4.7 (m, 1H, OCHO), 5.1–5.9 (m, 2H, CH=CH), 7.08 (br.s, 1H, C=CH—N).

EXAMPLE 18

Synthesis of 2-(N,N-dimethylaminomethylene)-3-[3-(tetrahydropyran-2-yloxy)-1-trans-octenyl]-4-(tetrahydropyran-2-yloxy)cyclopentanone (No. 136)

The same procedure as in Example 17 was repeated except that 273 mg (1.5 mmoles) of 4-(tetrahydropyran-2-yloxy)-2-cyclopentenone was used instead of the 2-cyclopentenone. Thus, 235 mg (yield 37%) of the captioned compound was obtained.

The properties of the product were as follows:

Rf(alumina; benzene/ethyl acetate=1/1 as a developing solvent): 0.30.

IR(liquid film): 1680 cm$^{-1}$(C=O), 1580 cm$^{-1}$(C=C).

NMR(CCl$_4$) δ: 0.8–1.0 (m, 3H, CH$_3$), 1.2–2.5 (m, 23H, CH$_2$ and CH), 3.05 (s, 6H, N(CH$_3$)$_2$), 3.1–4.1 (m, 6H, CHOTHP and OCH$_2$CH$_2$), 4.4–4.8 (m, 2H, OCHO), 5.1–5.9 (m, 2H, CH=CH), 7.16 (br.s, 1H, C=CH—N).

EXAMPLE 19

Synthesis of 3-(3-t-butyldimethylsiloxy-1-cis-octenyl)-2-dimethoxymethyl-cyclopentanone (No. 138)

(1) 774 mg (2.1 mmoles) of 1-iodo-3-t-butyldimethylsiloxy-1-cis-octene-1 was dissolved in 15 ml of dry ether, and the solution was transferred to a reaction tube dried and purged with argon. The solution was cooled to −95° C., and with good stirring, 3.44 ml (4.2 mmoles) of t-butyllithium (1.22 M pentane solution.Aldrich) was quickly added. While raising the temperature of the mixture gradually from −95° C. to −78° C., it was stirred for 2.5 hours.

(2) In the meantime, 400 mg (2.1 mmoles) of cuprous iodide was taken into a 50 ml eggplant-shaped flask, and heated and dried under reduced pressure. The inside atmosphere of the flask was purged with argon, and 15 ml of dry ether was added. Then, 1.15 ml (4.62 mmoles) of n-butylphosphine was added. The mixture was stirred at room temperature for 15 minutes, and then cooled to −78° C. The cooled mixture was added to the product obtained in (1) above by means of a stainless steel tube.

(3) The resulting mixture was stirred at −78° C. for 40 minutes, and a solution of 164 mg (2.0 mmoles) of 2-cyclopentanone in 10 ml of dry ether was added dropwise over the course of 10 minutes. The mixture was stirred for one hour, and 0.24 ml (2.2 mmoles) of methyl orthoformate and then 0.26 ml (2.1 mmoles) of a boron trifluoride/ether complex was added dropwise. The mixture was stirred at −78° C. for 5 hours. The product was hydrolyzed with 10 ml of a saturated aqueous solution of ammonium chloride, and the aqueous layer was extracted twice with 5 ml of ether. The organic layers were combinex, and dried over anhydrous magnesium sulfate. The product was filtered and concentrated, and then subjected to silica gel column chromatography (30 g of ammonia-treated silica gel; hexane/ether=30/1 as an eluent) to afford 550 mg (yield 69%) of the captioned compound.

The properties of the product were as follows:
Rf(hexane/ether=1/1 as a developing solvent): 0.60.
IR(liquid film): 1740 cm$^{-1}$(C=O).
NMR(CCl$_4$)δ: 0.7–1.0 (3H, m, —CH$_3$), 0.87 (9H, s, —C(CH$_3$)$_3$), 1.05–1.8 (10H, m), 1.9–2.4 (4H, m), 3.29 (3H, s, —OCH$_3$), 3.38 (3H, s, —OCH$_3$), 4.3–4.6

(1H, m, —CHOSi—(Me$_2$)—t-Bu), 4.51 (1H, d, J=3.0 Hz, —CH(OMe), 5.0–5.45

(2H, m, 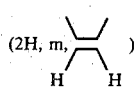 )

EXAMPLE 20

Synthesis of dl 2-(1-hydroxy-7-keto-8-oxanonyl)-3-[3-(t-butyldimethylsilyloxy)-1-trans-octenyl]-4-(t-butyldimethyl-silyloxy)-cyclopentanone (Nos. 140 and 142), and dl 2-(1-hydroxy-7-keto-8-oxanonyl)-3-(3-hydroxy-1-trans-octenyl)-4-hydroxycyclopentanone (Nos. 144, 146, 148 and 150)

Cuprous chloride (229 mg; 1.2 mmoles) was weighed into a 50 ml flask, and the inside atmosphere of the flask was purged with argon. Anhydrous ether (10 ml) was added, and then 0.60 ml (2.4 mmoles) of tri-n-butylphosphine was added at room temperature, followed by stirring for 10 minutes. The mixture was then cooled to −78° C., and a solution of 1.2 mmoles of dl 1-lithio-3-(t-butyldimethylsilyloxy)-trans-octene in a mixture of anhydrous ether and anhydrous hexane was added. The mixture was stirred at −78° C. for 30 minutes, and a solution of 212 mg (1.0 mmole) of dl 4-(t-butyldimethyl-silyloxy)-2-cyclopentenone in 5 ml of anhydrous ether was added dropwise. The mixture was stirred at −78° C. for 1 hour. Then, 0.15 ml of a boron trifluoride/ether complex was added, and the mixture was stirred at −78° C. for 10 minutes, and then at −40° C. for 20 minutes. Then, 5 ml of anhydrous tetrahydrofuran was added, and a solution of 221 mg (1.4 mmoles) of methyl 7-ketoheptanoate in 5 ml of anhydrous tetrahydrofuran was added. The mixture was stirred at −40° C. for 1.5 hours. The temperature of the mixture was gradually raised to room temperature, and the product was hydrolyzed with a saturated aqueous solution of ammonium chloride and extracted with ether. The organic layer was dried over anhydrous sodium sulfate, and concentrated under reduced pressure. The crude product was subjected to silica gel column chromatography. From the eluates resulting from elution with hexane/ethyl acetate (=9/1), two stereoisomers, dl 2-(1-hydroxy-7-keto-8-oxanonyl)-3-[3-(t-butyldimethylsilyloxy)-1-trans-octenyl]-4-(t-butyldimethylsilyloxy)cyclopentanone, were obtained in an amount of 59 mg (TLC: Rf=0.39; developing solvent hexane/ethyl acetate=4/1) and 35 mg (TLC: Rf=0.35; developing solvent hexane/ethyl acetate=4/1), respectively.

The properties of these products were as follows:
Stereoisomer (No. 140) having an Rf value of 0.39
IR(liquid film): 3470, 2960, 2945, 2870, 1741, 1461, 1436, 1404, 1388, 1360, 1251, 1196, 1170, 1104, 1002, 970, 938, 834, 772, 665 cm$^{-1}$.
NMR(CCl$_4$)δ0.85 (s,18H), 3.62 (s,3H), 3.85–4.3 /(m,2H), 5.46–5.70 (m,2H).
Stereoisomer (No. 142) having an Rf value of 0.35
IR(liquid film): 3470, 2960, 2940, 2870, 1742, 1464, 1438, 1410, 1378, 1360, 1258, 1100, 1006, 970, 938, 876, 836, 810, 778, 668 cm$^{-1}$.
NMR(CCl$_4$)δ0.88 (s, 18H), 3.60 (s, 3H), 3.4 (m, 1H) 3.7–4.3 (m, 2H), 5.4–5.7 (m, 2H).

These two compounds were each subjected to desilylation reaction in a customary manner (THF-water-AcOH=1:1:3; reacted at room temperature for 5 days). The solvent was removed by distillation under reduced pressure, and the product was separated by silica gel column chromatography (benzene/ethyl acetate=1/1) to afford dl 2-(1-hydroxy-7-keto-8-oxanonyl)-3-(3-hydroxy-1-trans-octenyl)-4-hydroxycyclopentane.

The properties of the products were as follows:
[Desilylation product of compound (No. 140)]

Compound having a larger Rf value (dl 15-epi-7-OHPGE$_1$ methyl ester) (No. 144); yield: 20%

NMR(CDCl$_3$)δ:0.89 (m, 3H), 1.1–1.8 (m, 16H), 2.0–2.95 (m,9H), 3.66 (s,3H), 3.6–3.85 (m, 1H), 3.9–4.25 (m, 2H), 5.4–5.9 (m, 2H).

Compound having a smaller Rf value (dl 7-OHPGE$_1$ methyl ester, No. 146); yield: 28%

NMR(CDCl$_3$)δ:0.89 (m, 3H), 1.0–1.7 (m, 16H), 1.9–2.9 (m, 6H), 3.05 (s, 3H, disappeared upon addition of D$_2$O), 3.66 (s, 3H), 3.5–3.8 (m, 1H), 3.9–4.2 (m, 2H), 5.45–5.7 (m, 2H).

[Desilylation product of compound No. 142]

Compound having a larger Rf value (dl 15-epi-7-OHPGE$_1$ methyl ester, No. 148); yield: 18%

(NMR(CDCl$_3$)δ:0.89 (m, 3H), 1.0–1.8 (m, 16H), 1.95–3.6 (m, 9H), 3.67 (s, 3H), 3.3–4.3 (m, 3H), 5.4–5.85 (m, 2H).

Compound having a smaller Rf value (dl 7-OHPGE$_1$ methyl ester, No. 150); yield: 14%

NMR(CDCl$_3$)δ:0.89 (m, 3H), 1.1–1.8 (m, 16H), 2.0–3.0 (m, 9H), 3.67 (s, 3H), 3.85–4.30 (m, 3H), 5.55–5.75 (m, 2H).

EXAMPLE 21

Synthesis of 2-(1-hydroxy-7-keto-8-oxanonyl)-3-[3(S)-(t-butyldimethylsilyloxy)-1-trans-octenyl]-4(R)-(t-butyldimethylsilyloxy) cyclopentanone (Nos. 152 and 154) and 2-(1-hydroxy-7-keto-8-oxanonyl)-3-[3(S)-hydroxy-1-trans-octenyl]-4(R)-hydroxycyclopentanone (Nos. 156 and 158)

Cuprous iodide (343 mg; 1.8 mmoles) was weighed into a 50 ml flask, and the inside atmosphere of flask was purged with argon. Anhydrous ether (15 ml) was added, and 0.9 ml (3.6 mmoles) of tri-n-butylphosphine was added at room temperature, followed by stirring for 10 minutes. The mixture was cooled to −78° C., and a solution of 1.8 mmoles of 1-lithio-3(S)-(t-butyldimethylsilyloxy)-trans-octene in a mixture of anhydrous ether and anhydrous hexane was added. The mixture was stirred at −78°0 C. for 30 minutes, and then, a solution of 318 mg (1.5 mmoles) of 4(R)-(t-butyldimethylsilyloxy)-2-cyclopentenone in 7 ml of anhydrous ether was added dropwise. The mixture was stirred at −78° C. for 1 hour. To the mixture was added 0.23 ml of a boron trifluoride-ether complex, and the mixture was stirred at −78° C. and then at −40° C. for 20 minutes. Anhydrous tetrahydrofuran (5 ml) was added, and a solution of 332 mg (2.1 mmoles) of methyl 7-keto-heptanoate in 7 ml of anhydrous tetrahydrofuran was added. The mixture was stirred at −40° C. for 1.5 hours. The temperature of the mixture was gradually raised to room temperature, and the product was hydrolyzed with a saturated aqueous solution of ammonium chloride, and extracted with ether. The organic layer was dried over anhydrous sodium sulfate, and concentrated under reduced pressure. The crude product was subjected to silica gel column chromatography. From the eluates resulting from elution with hexane/ethyl acetate (=9/1), two stereoisomers, 2-(1-hydroxy-7-keto-8-oxanonyl)-3-[3(S)-(t-butyldimethylsilyloxy)cyclopentanone, were obtained in an amount of 79 mg (TLC: Rf=0.39; developing solvent hexane/ethyl acetate=4/1; compound No. 152), and 75 mg (TLC: Rf=0.35; developing solvent hexane/ethyl acetate=4/1; compound No. 154), respectively.

The Rf value and spectral data of compound No. 152 correspond with those of compound No. 140 obtained in Example 20, and the Rf value and spectral data of compound No. 154, with those of compound No. 142 obtained in Example 20.

Then, the compounds Nos. 152 and 154 were each subjected to desilylation reaction to afford 2-(1-hydroxy-7-keto-8-oxanonyl)-3-[3(S)-hydroxy-1-trans-octenyl]-4(R)-hydroxycyclopentanone.

The Rf value and spectral data of 7-OHPGE$_1$ methyl ester (No. 156) obtained by desilylation of compound No. 152 correspond with those of compound No. 146 obtained in Example 20, and the Rf value and spectral data of an epimer of compound No. 156 (No. 158) obtained by desilylation of compound No. 154, with those of compound No. 150 obtained in Example 20.

EXAMPLE 22

By the method of Y. H. Lee et al. [Arch. Int. Pharmacodyn. Ther., 192, 370 (1971)], the inhibiting action of the compound No. 122 in Example 11 and compound No. 158 in Example 21 on the formation of ulcer in rats induced by indomethacin, a typical non-steroid anti-inflammatory agent, was evaluated. As shown in Table 1 below, this compound inhibited ulcer formation.

Male rats (Sprague Dawley species; body weight 240–270 g) were used in the experiment. These rats had been caused to fast for 24 hours in separate cages before the initiation of the experiment. Indomethacin was orally administered to these rats, and 6 hours later, they were killed. Formation of ulcer in the fundus part was examined by measuring the area of the ulcer-forming part under a microscope. The compounds Nos. 122 and 158 were each subcutaneously administered at the end of 30 minutes and 2 hours, respectively, after the administration of indomethacin. The ulcer formation inhibiting rate of these compounds against a predetermined dose of indomethacin was determined.

The indomethacin was administered as a 0.5 ml aqueous suspension (containing two drops of a Tween-type nonionic surfactant per 14 ml of water). The compounds Nos. 122 and 158 were given in the form of a solution in a phosphate buffer (pH 7.4).

Table 1 shows the inhibition, by compounds Nos. 122 and 158, of ulcer formation induced by indomethacin (20 mg/kg, peroral).

TABLE 1

| Compound | Dose (mg/kg, S.C.) | Number of rats | Ulcer formation (ulcer coefficient) Average value ± S.E.M. | Inhibiting rate (%) |
|---|---|---|---|---|
| None (control) | Zero | 12 | 20.3 ± 4.4 | 0 |
| (122) | 0.5 × 2 | 6 | 12.1 ± 4.1 | 40.4 |
| (158) | 0.5 × 2 | 5 | 15.8 ± 5.1 | 22.2 |

S.E.M. shows a standard error of the mean value

EXAMPLE 23

Activity of Inhibiting Platelet Aggregation In Vitro

The platelet aggregation inhibiting activities of test compounds including 7-hydroxy PGE$_1$ of this invention were tested using rabbit PRP. The results are shown in terms of their concentrations at 50% inhibition (IC$_{50}$) of platelet aggregation. As an aggregating agent, ADP-disodium salt having a final concentration of 5 μM was used.

Preparation of PRP, Test Compounds, and Aggregating Agent (1) Preparation of platelet-enriched plasma (PRP)

Citrated blood (consisting of 1 part by volume of 38% sodium citrate and 9 parts by volume of the blood) was prepared by taking blood from the ear veins of male rabbits having a body weight of 2.0 to 3.0 kg (white ordinary species). The citrated blood was centrifuged at 100 G for 10 minutes at room temperature, and the supernatant (PRP) was separated.

The PRP obtained was stored at room temperature, and used as early as possible. PRP stored for more than 4 hours after preparation was not used.

(2) Preparation of test drugs

Each test drug was dissolved in ethyl alcohol to a concentration of 10 mg/ml or 1 mg/ml, and diluted with physiological saline to adjust its concentration.

(3) Preparation of the aggregating agent

ADP Solution

ADP disodium salt (a product of Kyowa Hakko Kabushiki Kaisha) was dissolved in 0.1 M tris-HCl buffer (pH 7.8) to prepare a solution having a concentration of 50 μM (final concentration 5 μM).

Testing Method for Inhibition of Platelet Aggregation (1) Degree of platelet aggregation in a blank Physiological saline (25 μl) and 25 μl of the aggregating agent solution were added to 200 μl of PRP which had been warmed in a cuvette at 37° C. of an aggregometer to aggregate platelet. The aggregation curve was recorded for 3 minutes by an aggregometer (a product of Rika Denki Kabushiki Kaisha). The maximum degree of aggregation in this platelet aggregation was defined as the maximum degree of aggregation of the blank.

(2) Test for inhibition of platelet aggregation

The solution of test drug (25 μl) was added to 200 of PRP, and the mixture was pre-incubated for 2 minutes in a cuvette of an aggregometer. Then, 25 μl of the ADP disodium solution (50 μM) was added, and the aggregation curve was recorded for 3 minutes. The maximum degree of platelet aggregation within this period was measured, and the inhibiting rate was calculated from the following equation. The mimimum concentration (expressed as final concentration) of the drug whose inhibiting rate exceeded 50% was shown as an $IC_{50}$ value.

$$\text{Inhibiting rate (\%)} = \frac{\text{Maximum degree of aggregation in the drug-added system}}{\text{Maximum degree of aggregation of the blank}} \times 100$$

For details of the in vitro platelet aggregation inhibiting test, see H. M. Davis, J. Phyllis, K. Paul and W. Terry: Thromb. Res. 11, 217–226 (1977) and R. E. Anderson and J. G. Foulks: Thromb. Haemos. 36, 343–359 (1976).

The results are shown in Table 2.

TABLE 2

| Run No. | 7-Hydroxy PGE$_1$ methyl ester or its stereo-isomer | IC$_{50}$ (μg/ml) |
|---|---|---|
| 1 | No. 144 | >10 |
| 2 | No. 146 | 24.5 |
| 3 | No. 148 | >10 |
| 4 | No. 150 | >10 |

TABLE 2-continued

| Run No. | 7-Hydroxy PGE$_1$ methyl ester or its stereo-isomer | IC$_{50}$ (μg/ml) |
|---|---|---|
| 5 | No. 156 | 26.3 |
| 6 | No. 158 | 41.5 |

EXAMPLE 24

Formulation of tablets:

Tablets were prepared each of which had the following composition.

| | |
|---|---|
| Active ingredient | 200 mg |
| Lactose | 280 mg |
| Potato starch | 80 mg |
| Polyvinyl pyrrolidone | 11 mg |
| Magnesium stearate | 5 mg |
| | 576 mg |

The active ingredient, lactose and potato starch were mixed, and the mixture uniformly wetted with a 20% ethanol solution of polyvinyl pyrrolidone. The wet mixture was passed through a 2.0 mm-mesh sieve, and dried at 45° C., and again passed through a 1.5 mm-mesh sieve. The granules obtained were mixed with magnesium stearate, and the mixture compressed into tablets.

As representative active ingredients, compounds Nos. 156 and 158 were used respectively.

EXAMPLE 25

Formulation of capsules

Hard gelatin capsules were produced each of which had the following recipe.

| | |
|---|---|
| Active ingredient | 200 mg |
| Microcrystalline cellulose | 195 mg |
| Amorphous silica | 5 mg |
| | 400 mg |

The active ingredient in a finely divided form, the microcrystalline cellulose and the unpressed amorphous silica were fully mixed, and packed into hard gelatin capsules.

As representative active ingredients, compounds Nos. 156 and 158 were used respectively. No substantial trouble occurred during manufacture.

EXAMPLE 26

Ampoules were prepared each of which had a capacity of 5 ml and contained the following ingredients in the proportions indicated.

| | |
|---|---|
| Active ingredient | 200 mg |
| Polyethylene glycol 600 | 200 mg |
| Distilled water to make | 5 ml |

The active ingredient and polyethylene glycol were dissolved in water in an atmosphere of nitrogen. The solution was boiled, and cooled under a nitrogen atmosphere, and distilled. Pre-treated water was added to the solution to the desired capacity, and filtered aseptically. The above manufacturing operation was performed under scattered light. Filling of the solution was carried out in a stream of nitrogen, and sterilization was performed by heating at 121° C. for 20 minutes.

As representative active ingredients, compounds Nos. 156 and 158 were used.

EXAMPLE 27

Production of 7-hydroxyPGE$_1$-cyclodextrin inclusion compound

Ten milligrams of 7-hydroxyPGE$_1$ was dissolved in 0.1 ml of ethanol, and the solution was added to a solution of 15 mg of β-cyclodextrin in 0.2 ml of water. The mixture was stirred at room temperature for 10 minutes. The resulting mixture was concentrated under reduced pressure to afford 13 mg of a 7-hydroxyPGE$_1$-β-cyclodextrin inclusion compound. The product contained 6% of 7-hydroxyPGE$_1$.

What we claim is:

1. 7-Hydroxyprostaglandine E$_1$, or a stereoisomer thereof, or a protected derivative thereof, having the following formula (5)-c-1

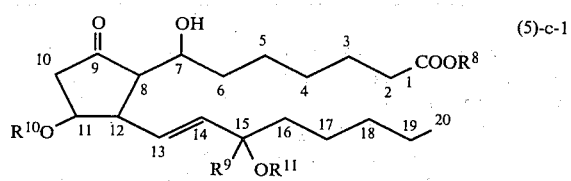

wherein R$^8$ represents a hydrogen atom, a methyl group or an ethyl group, R$^9$ represents a hydrogen atom or a methyl group, and R$^{10}$ and R$^{11}$ are identical or different, and each represents a hydrogen atom, a tetrahydropyranyl group or a t-butyldimethylsilyl group.

2. The compound of claim 1 having the following formula (5)-c-1′

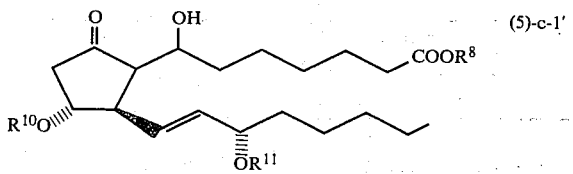

wherein R$^8$, R$^{10}$ and R$^{11}$ are as defined.

3. The compound of claim 1 having the following formula (5)-c-1″

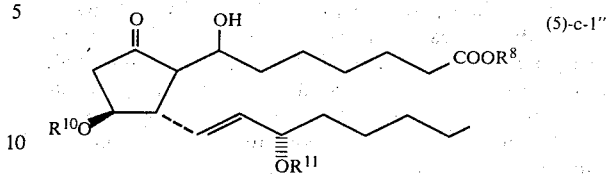

wherein R$^8$, R$^{10\ or\ 11}$ and R$^{11}$ are as defined.

4. The compound of claim 1 having the following formula (5)-c-1‴

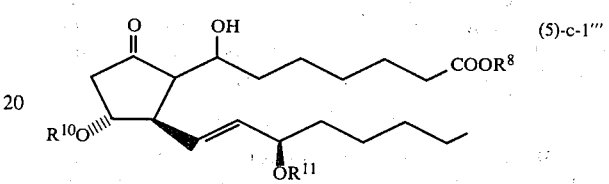

wherein R$^8$, R$^{10}$ and R$^{11}$ are as defined.

5. An anti-thrombotic composition comprising a pharmaceutically effective amount of 7-hydroxyprostaglandin E, or its stereoisomer of the following formula (5)-c-1⁗

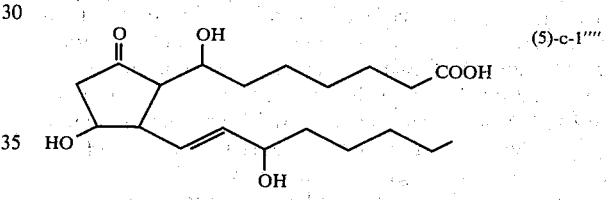

and a pharmaceutically acceptable carrier.

6. The anti-thrombotic composition of claim 5 in which said 7-hydroxyprostaglandin E$_1$ or its stereoisomer is included as an inclusion compound with cyclodextrin.

* * * * *

UNITED STATES PATENT AND TRADEMARK OFFICE
CERTIFICATE OF CORRECTION

PATENT NO. : 4,315,032
DATED : February 9, 1982
INVENTOR(S) : Ryoji NOYORI, Masaaki SUZUKI and Seizi KUROZUMI It is certified that error appears in the above—identified patent and that said Letters Patent is hereby corrected as shown below:

On the Title page Item [73] the Assignee should be:
Teijin Limited, Osaka, Japan Signed and Sealed this First Day of June 1982

[SEAL]

Attest:

GERALD J. MOSSINGHOFF

Attesting Officer   Commissioner of Patents and Trademarks